(12) United States Patent
Hussain et al.

(10) Patent No.: US 12,208,384 B2
(45) Date of Patent: Jan. 28, 2025

(54) ANALYTE DETECTION APPARATUS

(71) Applicant: Defense Diagnostics Inc., Plano, TX (US)

(72) Inventors: Ahmad Hussain, Marina Del Rey, CA (US); Jeremy Ridley, Philadelphia, PA (US); Chris Kolb, Philadelphia, PA (US); Justin Bechstein, Philadelphia, PA (US); Ayan Bhandari, Redwood City, CA (US); Stefan Grady Foulstone, San Francisco, CA (US); Rose Olivieri, Philadelphia, PA (US)

(73) Assignee: Defense Diagnostics Inc., Plano, TX (US)

( * ) Notice: Subject to any disclaimer, the term of this patent is extended or adjusted under 35 U.S.C. 154(b) by 0 days.

(21) Appl. No.: 18/612,468

(22) Filed: Mar. 21, 2024

(65) Prior Publication Data

US 2024/0316546 A1  Sep. 26, 2024

Related U.S. Application Data

(60) Provisional application No. 63/531,853, filed on Aug. 10, 2023, provisional application No. 63/454,305, filed on Mar. 23, 2023.

(51) Int. Cl.
*B01L 3/00* (2006.01)
(52) U.S. Cl.
CPC ..... *B01L 3/5023* (2013.01); *B01L 2200/0689* (2013.01); *B01L 2300/042* (2013.01);
(Continued)
(58) Field of Classification Search
None
See application file for complete search history.

(56) References Cited

U.S. PATENT DOCUMENTS 10,119,968 B2 * 11/2018 Lansing ................ B01L 3/5023
11,478,788 B1 * 10/2022 Leddon .............. G01N 33/9486
(Continued)

FOREIGN PATENT DOCUMENTS

WO   2012078455 A1   6/2012

OTHER PUBLICATIONS

International Search Report and Written Opinion, PCT/US2024/020986, mailed May 28, 2024.

*Primary Examiner* — Lore R Jarrett
(74) *Attorney, Agent, or Firm* — The Myers Law Group; Justin G. Sanders

(57) ABSTRACT

An analyte detection apparatus is disclosed and configured for testing a substance for the presence or absence of at least one target analyte. In at least one embodiment, a housing provides a mixing chamber and a testing chamber in selective fluid communication with the mixing chamber. During use of the apparatus, an end cap is disengaged from the housing, a volume of the substance is collected via a collection scoop provided by the end cap, the end cap is re-engaged with the housing, thereby introducing the substance from the collection scoop into the mixing chamber, the substance is mixed with a delivery fluid within the mixing chamber, and a mixing valve is rotated into an open position, allowing the substance to travel into the testing chamber and come into contact with a test medium, with a resulting visual indication from the test medium being viewable via a result window.

19 Claims, 13 Drawing Sheets

(52) U.S. Cl.
CPC .......... *B01L 2300/0825* (2013.01); *B01L 2300/0858* (2013.01); *B01L 2300/0867* (2013.01); *B01L 2400/0622* (2013.01)

(56) References Cited

U.S. PATENT DOCUMENTS

| | | |
|---|---|---|
| 2003/0049833 A1* | 3/2003 | Chen ............ B01L 7/525 |
| | | 435/288.2 |
| 2008/0260581 A1 | 10/2008 | Rosman et al. |
| 2019/0187162 A1* | 6/2019 | Shastry ........... G01N 21/6445 |
| 2020/0200738 A1 | 6/2020 | Sundvor et al. |
| 2021/0016269 A1 | 1/2021 | Gilboa-Geffen et al. |

* cited by examiner

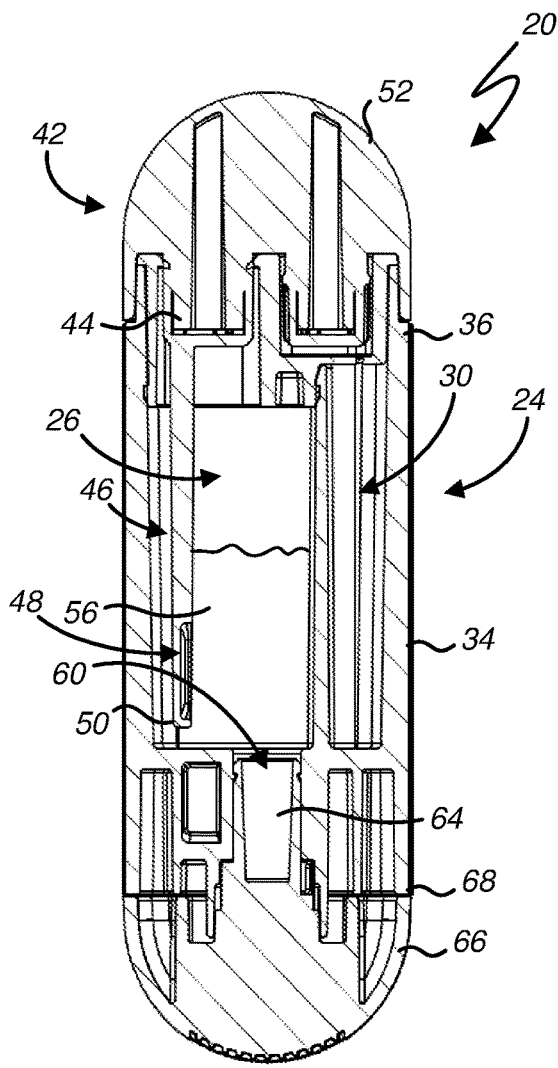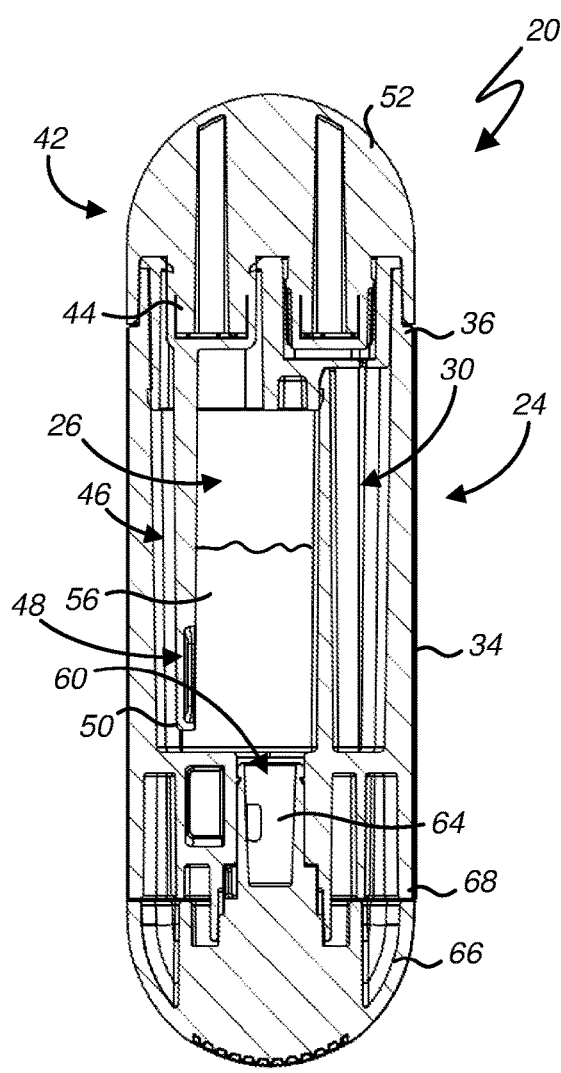
Fig. 3A
Fig. 3B

ANALYTE DETECTION APPARATUS

RELATED APPLICATIONS

This application claims priority and is entitled to the filing dates of U.S. provisional application Ser. No. 63/454,305, filed on Mar. 23, 2023, and U.S. provisional application Ser. No. 63/531,853, filed on Aug. 10, 2023. The contents of the aforementioned applications are incorporated herein by reference.

BACKGROUND

The subject of this patent application relates generally to diagnostic devices, and more particularly to an analyte detection apparatus configured for testing a substance for the presence or absence of an at least one target analyte.

Applicant hereby incorporates herein by reference any and all patents and published patent applications cited or referred to in this application.

By way of background, the rapid and accurate detection of visible and invisible analytes, including target molecules and microorganisms, is critical for many areas of research, environmental assessment, food safety, medical diagnosis, air quality assessment, homeland security, illicit drug identification, and warfare. In fact, diagnostic assays of biological compounds have become routine for a variety of applications, including medical diagnosis, forensic toxicology, pre-employment, insurance screening, and foodborne pathogen testing.

Industrial demand for low-cost, sensitive, rapid assays has caused the development of many testing systems and formats. These include, but are not limited to, lateral flow tests (e.g., lateral flow strips) for detecting analytes of interest (hereinafter referred to as "target analytes"). A typical lateral flow test utilizes the concept of lateral liquid or suspension flow in order to transport a given sample to the test. The benefits of lateral flow tests include a user-friendly format, rapid results, long-term stability over a wide range of climates, and relatively low cost to manufacture. Most lateral flow tests are directed to fluid samples and may require several separate materials or parts in a kit in order to perform and/or optimize detection of a target analyte. Known lateral flow tests require some means for collecting the sample and then a means of transferring the sample to the lateral flow strip, wherein the sample then travels up the lateral flow strip, and if the target analyte is present, binds to available antibodies which causes a reaction that can be visually detected on the test strip. Applying this technology to surface, air and fluid testing has been problematic, resulting in cumbersome testing procedures that have limitations.

Additional materials that can be provided with a lateral flow test include a separate vial containing a reagent, buffer solution or water to start the lateral flow reaction, and a wick or eye dropper to transport the sample to the test strip. As such, many of these lateral flow tests involve at least two separate components—one component for collecting the sample, and another component for testing the sample—along with multiple steps to perform the test. Thus, these known lateral flow tests tend to be cumbersome to use while mobile, in the field, or on the go—i.e., without a clean environment having sufficient space/surface area to arrange the various components and perform the test. As a result, these known lateral flow tests also tend to suffer from operator/collector error.

Accordingly, there remains a need for an analyte detection apparatus configured for creating a compact, controlled, self-contained environment capable of quickly and easily collecting, preparing and testing a substance for the presence or absence of an at least one target analyte. Aspects of the present invention fulfill these needs and provide further related advantages as described in the following summary.

It should be noted that the above background description includes information that may be useful in understanding aspects of the present invention. It is not an admission that any of the information provided herein is prior art or relevant to the presently claimed invention, or that any publication specifically or implicitly referenced is prior art.

SUMMARY

Aspects of the present invention teach certain benefits in construction and use which give rise to the exemplary advantages described below.

The present invention solves the problems described above by providing an analyte detection apparatus configured for testing a substance for the presence or absence of an at least one target analyte. In at least one embodiment, a housing of the apparatus provides a mixing chamber, a testing chamber and a scoop storage chamber positioned within the housing. The mixing chamber is sized and configured for temporarily storing a volume of the substance and a volume of a delivery fluid. The testing chamber is in selective fluid communication with the mixing chamber, the testing chamber sized and configured for containing a test medium therewithin, the test medium configured for visually indicating the presence or absence of the at least one target analyte within the substance. A first end of the housing provides a first chamber opening in fluid communication with the scoop storage chamber and a second chamber opening in fluid communication with the mixing chamber, the first and second chamber openings providing access to the scoop storage chamber and mixing chamber, respectively. An end cap is sized and configured for removable engagement with the first end of the housing. An elongate collection scoop extends substantially perpendicularly from an engagement end of the end cap and providing an at least one substance receptacle sized and configured for receiving an appropriate volume of the substance. The end cap is configured for removable engagement with the first end of the housing in each of a first cap orientation—wherein the collection scoop extends through the first chamber opening so as to be positioned within the scoop storage chamber—and a second cap orientation—wherein the collection scoop extends through the second chamber opening so as to be positioned within the mixing chamber. The mixing chamber provides a mixing aperture, while the testing chamber provides a testing aperture in selective fluid communication with the mixing aperture. A mixing valve is positioned inline between the mixing aperture and the testing aperture within the housing, the mixing valve rotatably engaged with the housing and configured for selectively rotating between one of an open position—wherein the mixing valve is circumferentially rotated relative to the housing so as to place the mixing aperture in fluid communication with the testing aperture, allowing an appropriate volume of the substance to travel through each of the mixing aperture and testing aperture and into the testing chamber—and a closed position—wherein the mixing valve is circumferentially rotated relative to the housing so as to obstruct fluid communication between the mixing aperture and testing aperture. The housing and testing chamber cooperate to provide an at least one result window positioned and configured for providing visual access into the testing chamber during use of the apparatus. During use of the apparatus, with the end cap engaged with the first end of the housing in the first cap orientation, the end cap is disengaged from the first end of the housing, an appropriate volume of the substance is collected via the at least one substance receptacle of the collection scoop, the end cap is re-engaged with the first end of the housing in the second cap orientation, thereby introducing the volume of substance from the collection scoop into the mixing chamber, the substance is mixed with the delivery fluid within the mixing chamber, and the mixing valve is rotated into the open position, allowing an appropriate volume of the substance to travel into the testing chamber and come into contact with the test medium, with a resulting visual indication from the test medium being viewable via the at least one result window.

In at least one alternate embodiment, a housing provides a mixing portion and a testing portion. The mixing portion defines an internal mixing chamber sized and configured for temporarily storing a volume of the substance and a volume of a delivery fluid. A first end of the mixing portion provides an inlet aperture in fluid communication with the mixing chamber, the inlet aperture sized and configured for allowing the volume of the substance to pass therethrough and into the mixing chamber. A collection scoop is positioned within the first end of the mixing portion and configured for moving between one of an open position—wherein the collection scoop is oriented so as to assist in the collection of the volume of the substance therewithin, and subsequently move the collected volume of the substance through the inlet aperture and into the mixing chamber—and a closed position—wherein the collection scoop is oriented so as to create a fluid-tight seal with the first end of the mixing portion, thereby preventing any of the volume of the substance or delivery fluid from unintentionally escaping through the inlet aperture. An opposing second end of the mixing portion provides an outlet aperture in fluid communication with the mixing chamber. The testing portion is rotatably engaged with the second end of the mixing portion, so as to be circumferentially rotatable relative to the mixing portion. The testing portion defines an internal testing chamber sized and configured for containing a test medium therewithin, the test medium configured for visually indicating the presence or absence of the at least one target analyte within the substance. The testing portion provides a testing aperture in fluid communication with the testing chamber. The testing chamber is configured for moving between one of an open position—wherein the testing portion is circumferentially rotated relative to the mixing portion so as to place the outlet aperture of the mixing portion in fluid communication with the testing aperture of the testing portion, allowing an appropriate volume of the substance to travel through each of the outlet aperture and testing aperture and into the testing chamber—and a closed position—wherein the testing portion is circumferentially rotated relative to the mixing portion so as to obstruct the outlet aperture, thereby cutting off fluid communication and creating a fluid-tight seal between the mixing chamber and the testing chamber. The testing portion also provides an at least one result window positioned and configured for providing visual access into the testing chamber during use of the apparatus. During use of the apparatus, with the testing portion in the closed position, the collection scoop is moved into the open position, the volume of the substance is collected and inserted into the mixing chamber, the collection scoop is moved into the closed position, the substance is mixed with the delivery fluid, and the testing portion is moved into the open position, allowing an appropriate volume of the substance to travel into the testing chamber and come into contact with the test medium, with a resulting visual indication from the test medium being viewable via the at least one result window.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings:

FIGS. 3A and 3B are cross-sectional views taken along line 3-3 of FIG. 1;

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION

Figure 1:
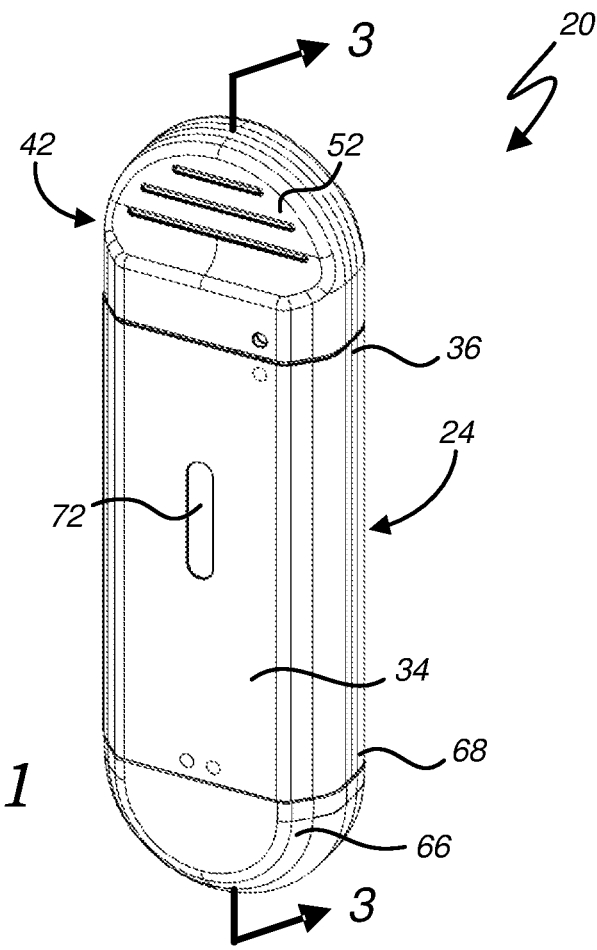
FIGS. 1 and 2 are perspective views of an exemplary analyte detection apparatus, in accordance with at least one embodiment.
Figure 2:
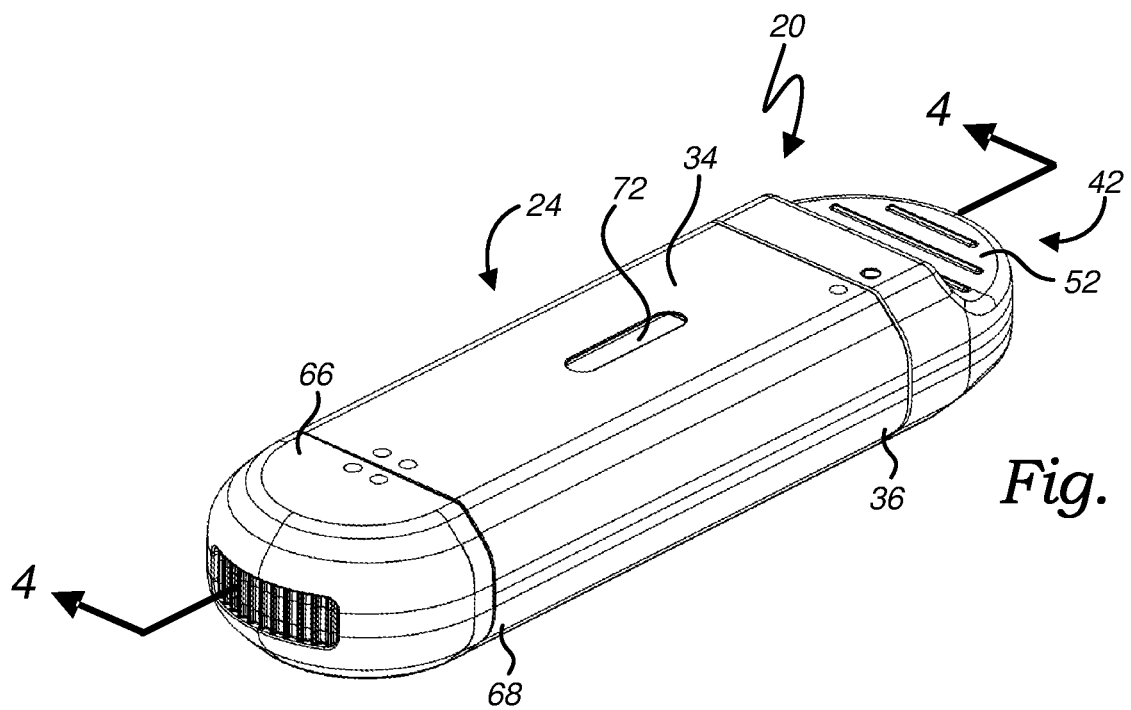

Turning now to FIGS. 1 and 2, there are shown perspective views of an exemplary analyte detection apparatus 20 configured for testing a substance 22 (FIG. 8) for the presence or absence of an at least one target analyte, in accordance with at least one embodiment. In that regard, it should be noted that while the apparatus 20 might be shown and described herein in certain specific contexts—such as the context of testing substances 22 for drugs of abuse (such as fentanyl, for example)—the apparatus 20 should not be read as being so limited. In further embodiments, the apparatus 20 may be configured for testing any substance 22 (solid, liquid or gas) for the presence or absence of virtually any target analyte, now know or later developed—including but in no way limited to pathogens or biomarkers in humans or animals, contaminants in water supplies, medications, foodstuffs, animal feeds, explosives, industrial waste, etc.

Figure 4:
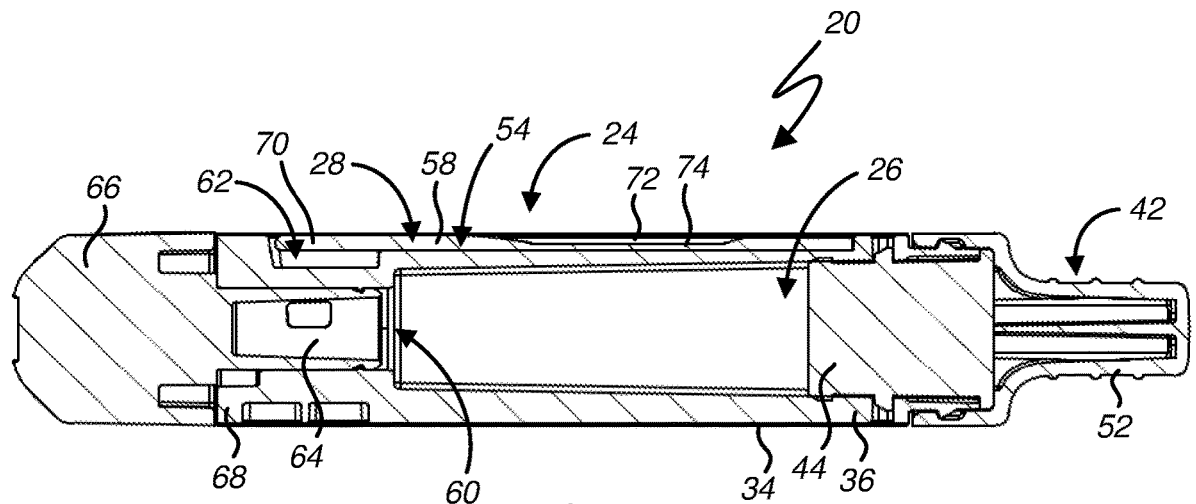
FIG. 4 is a cross-sectional view taken along line 4-4 of FIG. 2.

In at least one embodiment, as best illustrated in FIGS. 3A, 3B and 4, the apparatus 20 comprises a housing 24 that provides an internal mixing chamber 26, an internal testing chamber 28 in selective fluid communication with the mixing chamber 26, and a scoop storage chamber 30, as discussed further below. In at least one embodiment, the housing 24 is roughly the size of a standard lipstick or lip balm container. Additionally, in at least one embodiment, an outer surface of a sidewall 34 of the housing 24 provides a relatively planar surface positioned and configured for preventing the housing 24 from unintentionally rolling when placed on an uneven surface. However, in further embodiments, the housing 24 may take on any other sizes, shapes and/or dimensions, now known or later developed, so long as the apparatus 20 is capable of substantially carrying out the functionality described herein.

Figure 11:
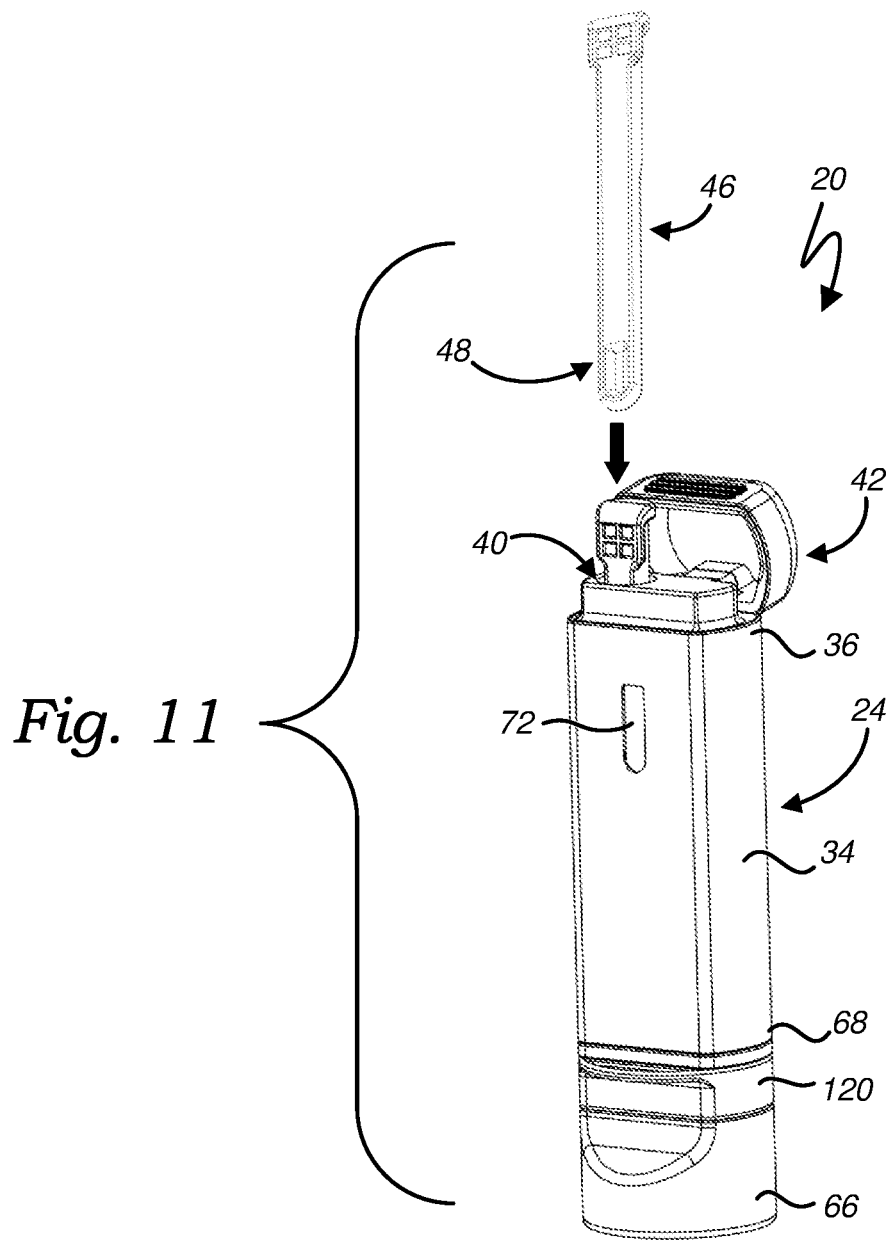
FIG. 11 is a further perspective view thereof, illustrating the insertion of an exemplary collection scoop into a mixing chamber of the apparatus, in accordance with at least one embodiment.

In at least one embodiment, the mixing chamber 26 is positioned substantially adjacent to the scoop storage chamber 30 within the housing 24. In at least one such embodiment, the mixing chamber 26 and scoop storage chamber 30 are positioned in a substantially side-by-side arrangement within the housing 24. Additionally, in at least one embodiment, a first end 36 of the housing 24 provides a first chamber opening 38 in fluid communication with the scoop storage chamber 30 and a substantially adjacent second chamber opening 40 in fluid communication with the mixing chamber 26, with the first and second chamber openings 38 and 40 providing access to the scoop storage chamber 30 and mixing chamber 26, respectively. In at least one embodiment, the apparatus 20 further provides an end cap 42 sized and configured for removable engagement with the first end 36 of the housing 24. In at least one embodiment, an engagement end 44 of the end cap 42 is frictionally engageable with the first end 36 of the housing 24, thereby providing a fluid-tight and pressurized seal therebetween and preventing the contents of the mixing chamber 26 from exiting the housing 24. In at least one such embodiment, the first end 36 of the housing 24 provides an O-ring, gasket or other type of sealing membrane positioned and configured for creating the fluid-tight seal between the engagement end 44 of the end cap 42 and one or both of the first and second chamber openings 38 and 40. However, in further embodiments, the apparatus 20 may utilize any other mechanisms or techniques, now known or later developed, capable of creating a fluid-tight seal between the engagement end 44 of the end cap 42 and one or both of the first and second chamber openings 38 and 40. In at least one embodiment, the end cap 42 is fully removably engageable with the housing 24. In at least one alternate embodiment, as best illustrated in FIG. 11, the end cap 42 is hingedly engaged with the housing 24.

Figure 7:
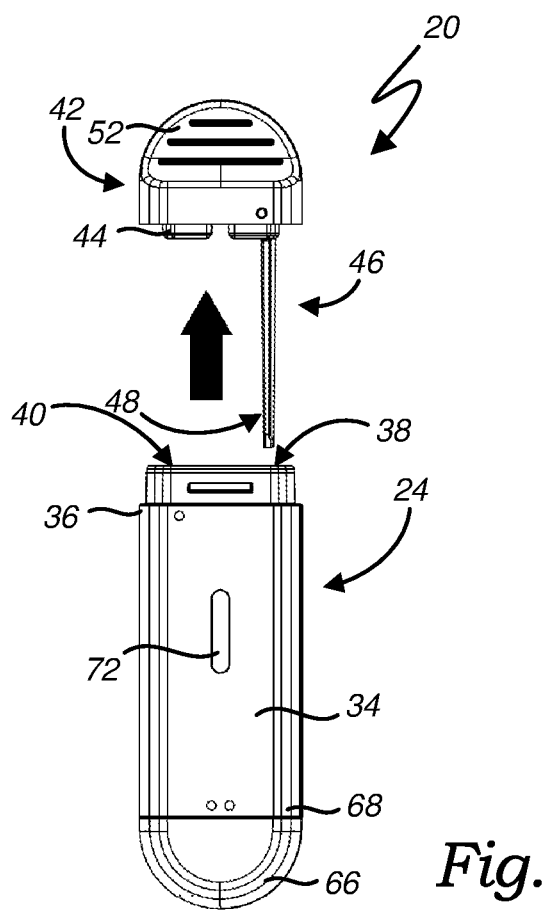
FIGS. 7-9 are further perspective views of the apparatus, illustrating an exemplary method for testing a substance for the presence or absence of an at least one target analyte, in accordance with at least one embodiment.
Figure 8:
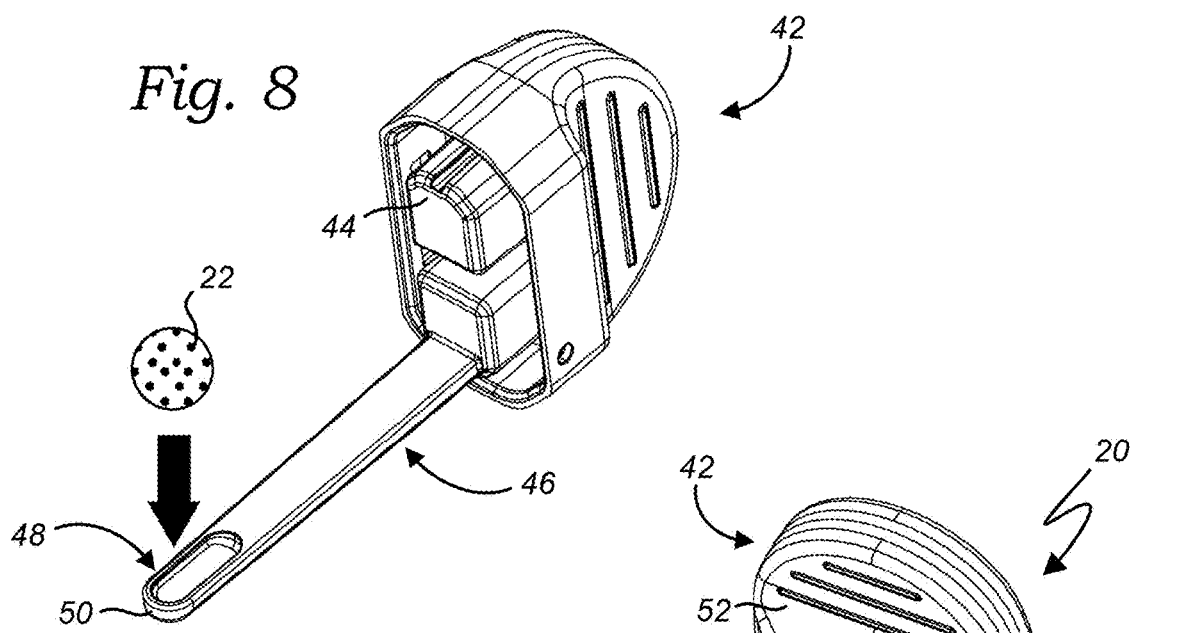

In at least one embodiment, as best illustrated in FIGS. 7 and 8, the end cap 42 provides an elongate collection scoop 46 extending substantially perpendicularly from the engagement end 44 of the end cap 42. The collection scoop 46 is positioned such that when the end cap 42 is engaged with the first end 36 of the housing 24 in a first cap orientation (FIG. 7), the collection scoop 46 extends through the first chamber opening 38 so as to be positioned within the scoop storage chamber 30; and when the end cap 42 is engaged with the first end 36 of the housing 24 in a second cap orientation (FIG. 9), the collection scoop 46 extends through the second chamber opening 40 so as to be positioned within the mixing chamber 26. Accordingly, in at least one such embodiment, the end cap 42 is bilaterally symmetrical, except for the collection scoop 46, thereby allowing the end cap 42 to be engaged with the first end 36 of the housing 24 in both the first cap orientation and the second cap orientation. In at least one embodiment, as best illustrated in FIG. 8, the collection scoop 46 provides an at least one substance receptacle 48 sized and configured for receiving an appropriate volume of the substance 22 to be tested. Accordingly, as discussed further below, the collection scoop 46 is configured for introducing a volume of the substance 22 to be tested into the mixing chamber 26 when the end cap 42 is engaged with the first end 36 of the housing 24 in the second cap orientation. In at least one embodiment, the at least one substance receptacle 48 is positioned proximal to a terminal end 50 of the collection scoop 46; however, in further embodiments, the at least one substance receptacle 48 may be positioned anywhere else on the collection scoop 46. In at least one alternate embodiment, as best illustrated in FIGS. 10 and 11, the collection scoop 46 is separate from the end cap 42, and is instead slidably engageable with a scoop slot 118 positioned on an exterior of the housing 24 and configured for storing the collection scoop 46 when it is not in use. Accordingly, in such embodiments, the scoop storage chamber 30 and first chamber opening 38 are omitted. In still further embodiments, the collection scoop 46 may be positioned elsewhere relative to the housing 24.

In at least one embodiment, the end cap 42 further provides a relatively flat grip portion 52, positioned substantially opposite to the engagement end 44, sized and configured for facilitating the handling and manual operation of the end cap 42, along with the apparatus 20 generally, during use. It should be noted that in further embodiments, each of the end cap 42, collection scoop 46 and grip portion 52 may take on any other sizes, shapes, dimensions and/or relative positions, now known or later developed, so long as the apparatus 20 is capable of substantially carrying out the functionality described herein. Similarly, in further embodiments, the at least one substance receptacle 48 may take on any other sizes, shapes, dimensions, configurations, quantities and/or relative positions, now known or later developed, so long as the apparatus 20 is capable of substantially carrying out the functionality described herein.

In at least one embodiment, as best illustrated in FIGS. 3A and 3B, the scoop storage chamber 30 is sized and configured for receiving the collection scoop 46 therewithin when the end cap 42 is engaged with the first end 36 of the housing 24 in the first cap orientation. As discussed further below, in at least one embodiment, the collection scoop 46 is positioned within the scoop storage chamber 30 prior to the apparatus 20 being used to test a given substance 22 for the presence or absence of at least one target analyte. Accordingly, in at least one such embodiment, the scoop storage chamber 30 is sized to approximate the dimensions of the collection scoop 46. However, in further embodiments, the scoop storage chamber 30 may take on any other sizes, shapes, dimensions, configurations and/or relative positions, now known or later developed, so long as the apparatus 20 is capable of substantially carrying out the functionality described herein. Additionally, in at least one embodiment, the scoop storage chamber 30 is devoid of any substances. In at least one alternate embodiment, the scoop storage chamber 30 is omitted, such that the housing 24 merely provides the mixing chamber 26, with the collection scoop 46 being positioned within the mixing chamber 26 when the end cap 42 is engaged with the first end 36 of the housing 24 in both the first cap orientation and the second cap orientation.

In at least one embodiment, the mixing chamber 26 is sized and configured for storing a volume of the substance 22 to be tested, while also being sized and configured for receiving the collection scoop 46 therewithin when the end cap 42 is engaged with the first end 36 of the housing 24 in the second cap orientation. Additionally, in at least one embodiment, as best illustrated in FIGS. 3A and 3B, where the substance 22 is a solid (such as a pill or portions of a pill, for example), the mixing chamber 26 is further configured for storing a volume of an appropriate reagent, buffer solution, water or other fluid configured for dissolving and aiding in the delivery of the substance 22 to a test medium 54 of the apparatus 20 (hereinafter collectively referred to generally as the "delivery fluid" 56 for simplicity purposes), as discussed further below. In at least one embodiment, the delivery fluid 56 is added to the mixing chamber 26 at the time of manufacturing the apparatus 20. In at least one alternate embodiment, the delivery fluid 56 is added to the mixing chamber 26 after the apparatus 20 has been manufactured and prior to the apparatus 20 being used to test a given substance 22 for the presence or absence of at least one target analyte—either before or after the substance 22 has been inserted into the mixing chamber 26. In at least one further alternate embodiment, the delivery fluid 56 is temporarily contained within a breakable fluid capsule (not shown) positioned within the mixing chamber 26. In at least one such embodiment, the sidewall 34 of the housing 24 (or a portion of the sidewall 34) is constructed out of a relatively resilient material, thereby allowing the housing 24 (and, in turn, the mixing chamber 26) to be temporarily radially collapsed inwardly in order to break the fluid capsule and release the delivery fluid 56 into the mixing chamber 26. In at least one alternate such embodiment, the housing 24 provides a mechanism (such as a spring-biased plunger, for example—though any other functionally sufficient mechanism, now known or later developed, may be substituted) configured for breaking the fluid capsule within the mixing chamber 26. In at least one embodiment, the sidewall 34 of the housing 24, along with at least a portion of the mixing chamber 26, is transparent or translucent, thereby providing visual access into the mixing chamber 26 during use of the apparatus 20. In at least one embodiment, as illustrated in FIG. 10, the housing 24 provides an at least one mixing window 124 positioned and configured for providing visual access into the mixing chamber 26, thereby allowing a user to visually confirm that the substance 22 has been properly mixed with the delivery fluid 56 during use of the apparatus 20.

As mentioned above, in at least one embodiment, the housing 24 provides a testing chamber 28 in selective fluid communication with the mixing chamber 26. In at least one embodiment, the testing chamber 28 is sized and configured for containing a test medium 54 therewithin, the test medium 54 configured for visually indicating the presence or absence of the at least one target analyte within the substance 22. In at least one embodiment, the test medium 54 is a lateral flow test strip 58. In at least one alternate embodiment, the test medium 54 is a volume of an appropriate reagent configured to react to the at least one target analyte. In still further embodiments, the test medium 54 may be any other type of test medium 54, now known or later developed, capable of visually indicating the presence or absence of the at least one target analyte within the substance 22.

Figure 5:
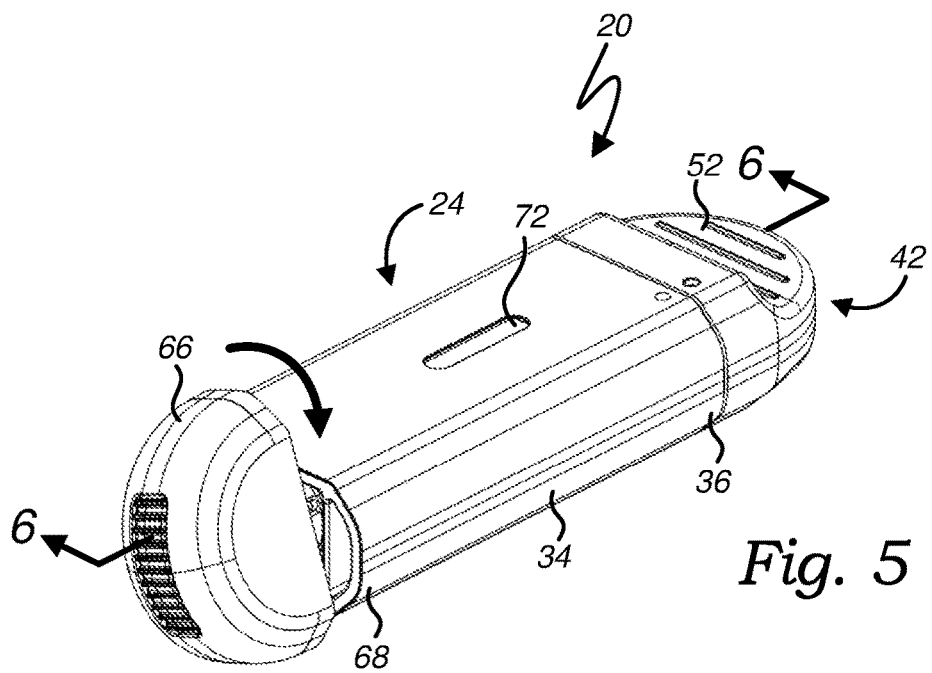
FIG. 5 is a further perspective view of the apparatus, in accordance with at least one embodiment.
Figure 6:
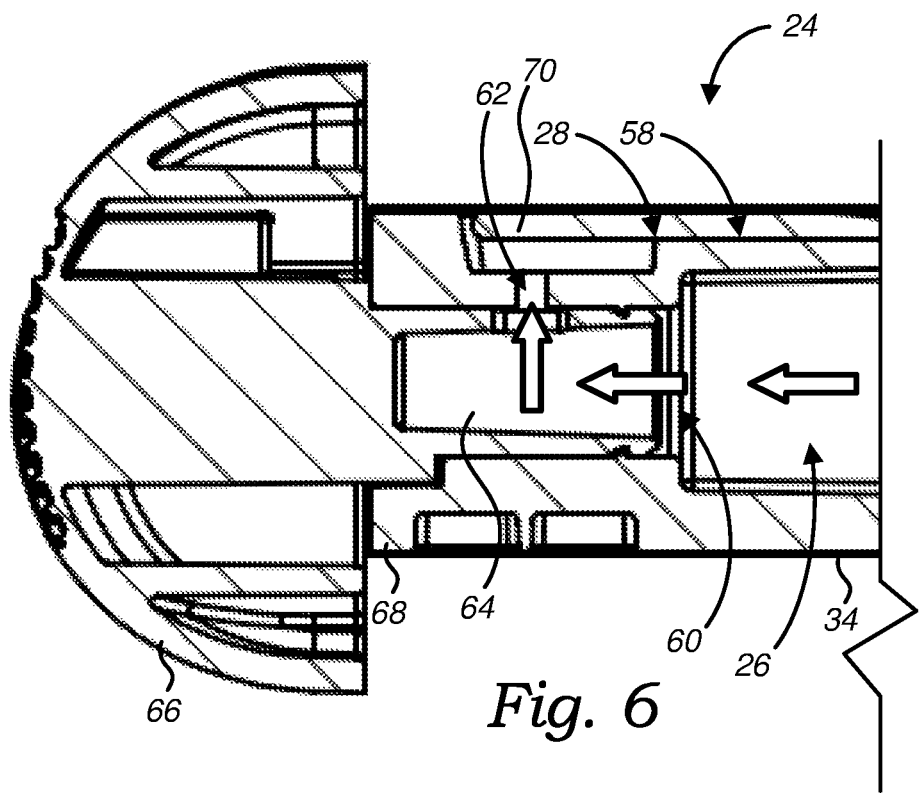
FIG. 6 is a partial cross-sectional view taken along line 6-6 of FIG. 5.

In at least one embodiment, as best illustrated in FIG. 6, the mixing chamber 26 provides a mixing aperture 60, while the testing chamber 28 provides a testing aperture 62, with the mixing aperture 60 and testing aperture 62 being in selective fluid communication with one another. Additionally, in at least one embodiment, as best illustrated in FIGS. 3A, 3B and 4, the housing 24 further provides a mixing valve 64 positioned inline between the mixing aperture 60 and the testing aperture 62. In at least one embodiment, the mixing valve 64 is rotatably engaged with the housing 24 and configured for selectively rotating between one of an open position (FIGS. 5 and 6)—wherein the mixing valve 64 is circumferentially rotated or twisted relative to the housing 24 so as to place the mixing aperture 60 in fluid communication with the testing aperture 62, allowing a volume of the substance 22 (along with the delivery fluid 56, where applicable) to travel through each of the mixing aperture 60 and testing aperture 62 and into the testing chamber 28—and a closed position (FIGS. 2 and 4)—wherein the mixing valve 64 is circumferentially rotated or twisted relative to the housing 24 so as to obstruct fluid communication between the mixing aperture 60 and testing aperture 62. In at least one such embodiment, one or both of the mixing aperture 60 and testing aperture 62 provides an O-ring, gasket or other type of sealing membrane positioned and configured for creating a fluid-tight seal between the mixing chamber 26 and the testing chamber 28 when the mixing valve 64 is in the closed position. However, in further embodiments, the apparatus 20 may utilize any other mechanisms or techniques, now known or later developed, capable of creating a fluid-tight seal between the mixing chamber 26 and the testing chamber 28 when the mixing valve 64 is in the closed position.

In at least one embodiment, the mixing valve 64 provides a valve knob 66 rotatably engaged with the housing 24 and in mechanical communication with the mixing valve 64, the valve knob 66 configured for enabling the mixing valve 64 to be manually rotated between the open position and closed position during use of the apparatus 20, as discussed further below. In at least one embodiment, the valve knob 66 is rotatably engaged with an opposing second end 68 of the housing 24. In at least one such embodiment, as best illustrated in FIG. 5, rotating the mixing valve 64 into the open position involves manually rotating the valve knob 66 approximately 90 degrees relative to the second end 68 of the housing 24. Additionally, in at least one such embodiment, as best illustrated in FIGS. 3A and 3B, rotating the mixing valve 64 back into the closed position involves manually rotating the valve knob 66 approximately 90 degrees in either direction relative to the second end 68 of the housing 24. In further embodiments, the valve knob 66 may be rotatably engaged elsewhere on the housing 24. Similarly, in further embodiments, the valve knob 66 and mixing valve 64 may each take on any other sizes, shapes, dimensions, configurations and/or relative positions, now known or later developed, so long as the apparatus 20 is capable of substantially carrying out the functionality described herein. In at least one embodiment, as best illustrated in FIG. 10, the apparatus 20 provides a valve lock 120 configured for preventing the valve knob 66 from being unintentionally rotated into the open position. In at least one such embodiment, the valve lock 120 is a clip having a keyed surface configured for removably mating with a corresponding clip recess 122 provided by the valve knob 66. Accordingly, in such embodiments, when the valve lock 120 is engaged with the clip recess 122, the valve knob 66 is physically prevented from rotating relative to the housing 24. In further embodiments, the valve lock 120 may take on any other configurations, now known or later developed, so long as the valve lock 120 is capable of preventing the valve knob 66 from being unintentionally rotated into the open position.

In at least one embodiment, one or both of the valve knob 66 and housing 24 provide an at least one position indicator configured for visually indicating the current position of the mixing valve 64—i.e., open position or closed position. In at least one such embodiment, the valve knob 66 and housing 24 provide corresponding position indicators, such that when the mixing valve 64 is in the open position, the position indicators on the valve knob 66 and housing 24 are linearly aligned with one another. In further embodiments, the at least one position indicator may take on any other sizes, shapes, dimensions, quantities and/or relative positions, now known or later developed, so long as the apparatus 20 is capable of substantially carrying out the functionality described herein. In at least one alternate embodiment, as best illustrated in FIGS. 2 and 5, the valve knob 66 itself is shaped for visually indicating the current position of the mixing valve 64.

In at least one embodiment, the test medium 54 is positioned substantially adjacent to the testing aperture 62 so as to come into contact with the substance 22 (along with the delivery fluid 56, where applicable) as it passes through the testing aperture 62 and enters the testing chamber 28 when the mixing valve 64 is in the open position. Thus, where the test medium 54 is a test strip 58, a sample pad 70 of the test strip 58 is positioned substantially adjacent to the testing aperture 62. In at least one embodiment, the testing chamber 28 and housing 24 further provides an at least one transparent or translucent result window 72 positioned and configured for providing visual access into the testing chamber 28 during use of the apparatus 20, in order to view the visual indication of the presence or absence of the at least one target analyte within the substance 22 as provided by the test medium 54. In that regard, it should be noted that the at least one result window 72 may take on any other sizes, shapes, dimensions, configurations and/or relative positions, now known or later developed—dependent at least in part on the test medium 54—so long as the apparatus 20 is capable of substantially carrying out the functionality described herein. Thus, in at least one embodiment, where the test medium 54 is a test strip 58, the at least one result window 72 is substantially aligned with a detection zone 74 of the test strip 58 (i.e., the portion of the test strip 58 containing each of a test line and a control line). In at least one embodiment, where the test medium 54 is a test strip 58 or other type of test medium 54 where the result portion of the test medium 54 (such as the detection zone 74 in the case of a test strip 58) must remain substantially dry, the testing chamber 28 defines a separate result chamber (not shown) that is substantially sealed off from a remaining portion of the testing chamber 28, within which the result portion of the test medium 54 is positioned, thereby preventing the substance 22 (along with the delivery fluid 56, where applicable) from flowing into the result chamber and saturating the result portion of the test medium 54.

Figure 9:
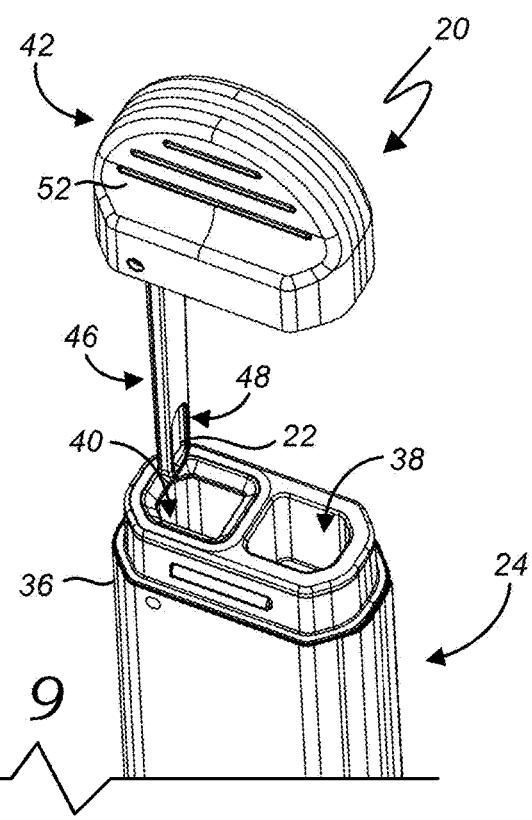
Figure 10:
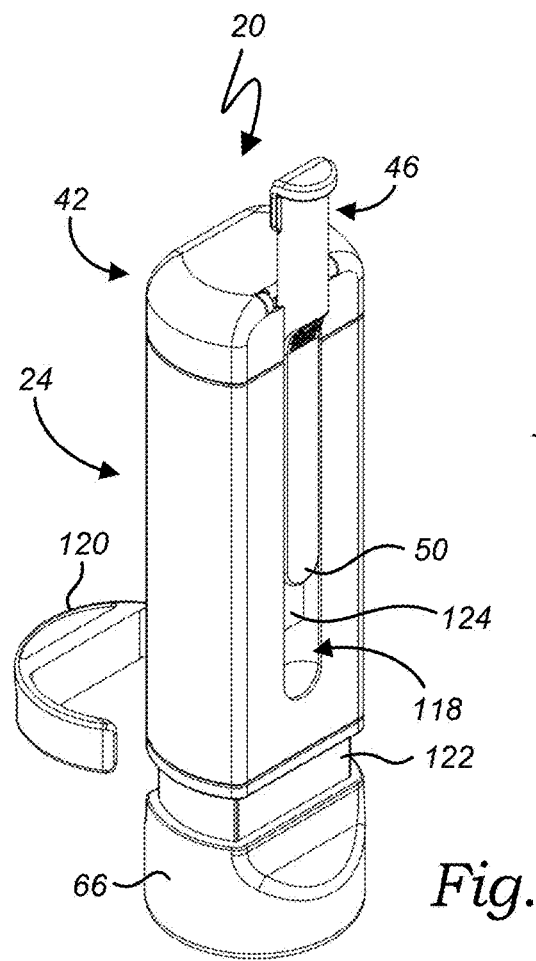
FIG. 10 is a perspective view of a further exemplary analyte detection apparatus, in accordance with at least one embodiment.
Figure 12:
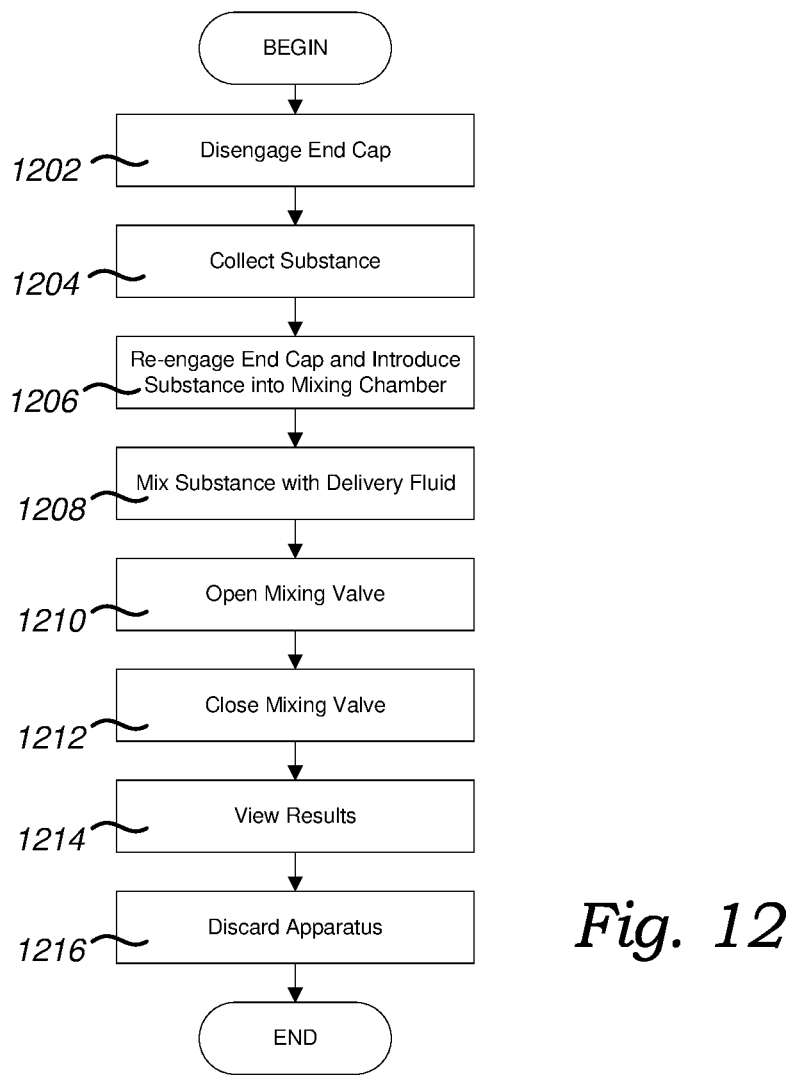
FIG. 12 is a flow diagram of an exemplary method for testing a substance for the presence or absence of an at least one target analyte, in accordance with at least one embodiment.

In at least one embodiment, as illustrated in FIGS. 7-9 along with the flow diagram of FIG. 12, during use of the apparatus 20, with the end cap 42 engaged with the first end 36 of the housing 24 in the first cap orientation, the end cap 42 is disengaged from the first end 36 of the housing 24 (FIG. 7) to gain access to the collection scoop 46 (1202). An appropriate volume of the substance 22 is collected via the at least one substance receptacle 48 of the collection scoop 46 (FIG. 8) (1204). With the volume of substance 22 positioned within the at least one substance receptacle 48 of the collection scoop 46, the end cap 42 is re-engaged with the first end 36 of the housing 24, but in the second cap orientation, thereby introducing the volume of substance 22 into the mixing chamber 26 (along with the delivery fluid 56, where applicable) (FIG. 9) (1206). In embodiments where the delivery fluid 56 is already positioned within the mixing chamber 26 prior to the introduction of the volume of substance 22, the housing 24 should be held in a substantially vertical orientation while the end cap 42 is disengaged so as to prevent the delivery fluid 56 from spilling out of the mixing chamber 26. In at least one alternate embodiment, where the delivery fluid 56 is contained within a breakable fluid capsule positioned within the mixing chamber 26, the fluid capsule is broken. In at least one embodiment, where delivery fluid 56 is present, the apparatus 20 is shaken so as to mix the volume of substance 22 with the delivery fluid 56 (1208)—and where the volume of substance 22 is solid, the volume of substance 22 is allowed time to sufficiently dissolve in the delivery fluid 56.

In at least one embodiment, the mixing valve 64 is then rotated into the open position (FIG. 5) (1210). As mentioned above, in at least one embodiment, the engagement end 44 of the end cap 42 is frictionally engageable with the first end 36 of the housing 24, thereby providing a fluid-tight and pressurized seal therebetween. Thus, the act of the end cap 42 being re-engaged with the first end 36 of the housing 24 in step 1206 causes the mixing chamber 26 to be pressurized. Accordingly, upon the mixing valve 64 being rotated into the option position in step 1210, the pressure within the mixing chamber 26 causes an appropriate volume of the substance 22 (along with the delivery fluid 56, where applicable) to travel into the test chamber (via the mixing valve 64) and come into contact with the test medium 54. In at least one embodiment, the apparatus is held in a substantially vertical orientation during step 1210 and for a predetermined period of time thereafter (such as 10-15 seconds, for example) to better ensure that an appropriate volume of the substance 22 (along with the delivery fluid 56, where applicable) comes into contact with the test medium 54. In at least one embodiment, after an appropriate volume of the substance 22 (along with the delivery fluid 56, where applicable) comes into contact with the test medium 54, the mixing valve 64 is rotated back into the closed position (1212). In at least one embodiment, the apparatus 20 is placed on a generally horizontally-oriented surface with the result window 72 facing upward (FIG. 2), and the results of the test are eventually viewable via the result window 72

(1214). In at least one embodiment, the apparatus 20 is designed for one-time use, such that the apparatus 20 may be discarded after the results of the test are viewed (1216). Thus, in at least one embodiment, the apparatus 20 is a small, self-contained, user-friendly device capable of quickly and easily testing the substance 22 for the presence or absence of one or more target analytes—both at work or at home, as well as while on the go.

Figure 13:
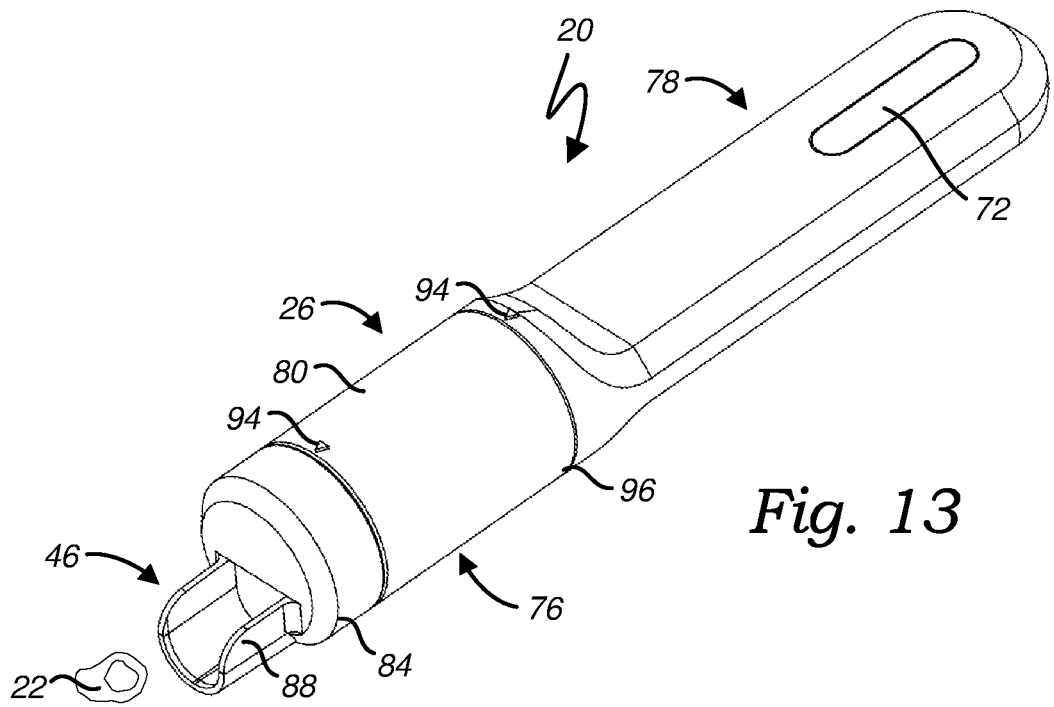
FIG. 13 is a perspective view of a further exemplary analyte detection apparatus, in accordance with at least one embodiment.

In at least one alternate embodiment, as illustrated in FIG. 13, the apparatus 20 comprises a housing 24 that provides a mixing portion 76 and a testing portion 78 rotatably engaged with the mixing portion 76, as discussed further below. In at least one embodiment, the housing 24 is roughly the size of a standard lipstick or lip balm container. Additionally, in at least one embodiment, a circumferential sidewall 80 of the mixing portion 76 provides a relatively planar surface positioned and configured for preventing the housing 24 from unintentionally rolling when placed on an uneven surface. In at least one embodiment, the testing portion 78 is configured as a relatively flat, long handle to facilitate the handling and manual operation of the apparatus 20 during use. However, in further embodiments, the housing 24 (including each of the mixing portion 76 and testing portion 78) may take on any other sizes, shapes and/or dimensions, now known or later developed, so long as the apparatus 20 is capable of substantially carrying out the functionality described herein.

In at least one embodiment, the mixing portion 76 defines the internal mixing chamber 26 sized and configured for temporarily storing a volume of the substance 22 to be tested. Additionally, in at least one embodiment, where the substance 22 is a solid (such as a pill or portions of a pill, for example), the mixing chamber 26 is further configured for temporarily storing a volume of delivery fluid 56, as discussed further below. In at least one embodiment, the delivery fluid 56 is temporarily contained within a breakable fluid capsule 82 positioned within the mixing chamber 26. In at least one such embodiment, the sidewall 80 of the mixing portion 76 (or a portion of the sidewall 80) is constructed out of a relatively resilient material, thereby allowing the mixing portion 76 (and, in turn, the mixing chamber 26) to be temporarily radially collapsed inwardly in order to break the fluid capsule 82 and release the delivery fluid 56 into the mixing chamber 26, as discussed further below. In at least one alternate embodiment, the mixing portion 76 provides a mechanism (such as a spring-biased plunger, for example—though any other functionally sufficient mechanism, now known or later developed, may be substituted) configured for breaking the fluid capsule 82. In at least one further alternate embodiment, rather than being positioned within a fluid capsule 82, the delivery fluid 56 is simply added to the mixing chamber 26 after the substance 22 has been inserted into the mixing chamber 26. In at least one still further alternate embodiment, the delivery fluid 56 is positioned within the mixing chamber 26 prior to the substance 22 being inserted into the mixing chamber 26. In at least one embodiment, the sidewall 80 of the mixing portion 76 is transparent or translucent, thereby providing visual access into the mixing chamber 26 during use of the apparatus 20.

In at least one embodiment, a first end 84 of the mixing portion 76 provides an inlet aperture 86 in fluid communication with the mixing chamber 26, the inlet aperture 86 being sized and configured for allowing the substance 22 to pass therethrough and into the mixing chamber 26. Additionally, in at least one embodiment, the mixing portion 76 provides a collection scoop 46 positioned within the first end 84 of the mixing portion 76. In at least one embodiment, the collection scoop 46 is configured for moving between one of an open position—wherein the collection scoop 46 is oriented so as to assist in the collection of a volume of the substance 22 therewithin, and subsequently move the collected volume of the substance 22 through the inlet aperture 86 and into the mixing chamber 26—and a closed position—wherein the collection scoop 46 is oriented so as to create a fluid-tight seal with the first end 84 of the mixing portion 76, thereby preventing any of the substance 22 or delivery fluid 56 from unintentionally escaping through the inlet aperture 86.

Figure 14:
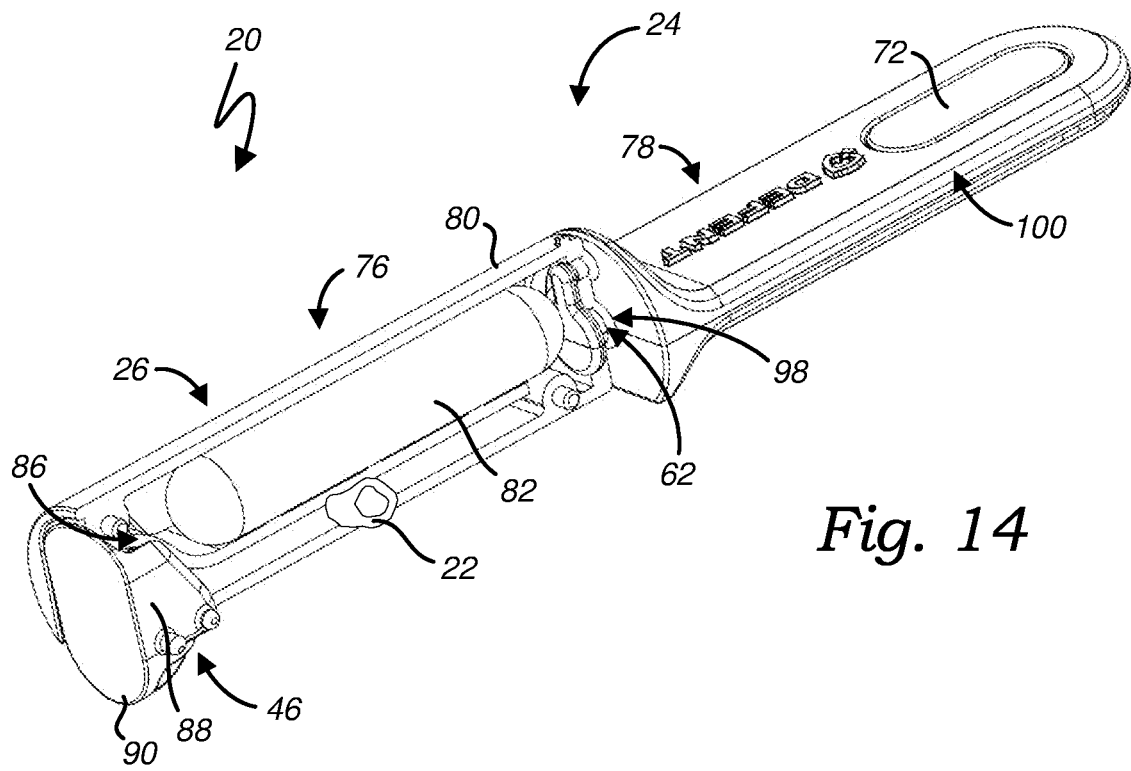
FIG. 14 is a longitudinal cross-sectional view thereof, in accordance with at least one embodiment.
Figure 15:
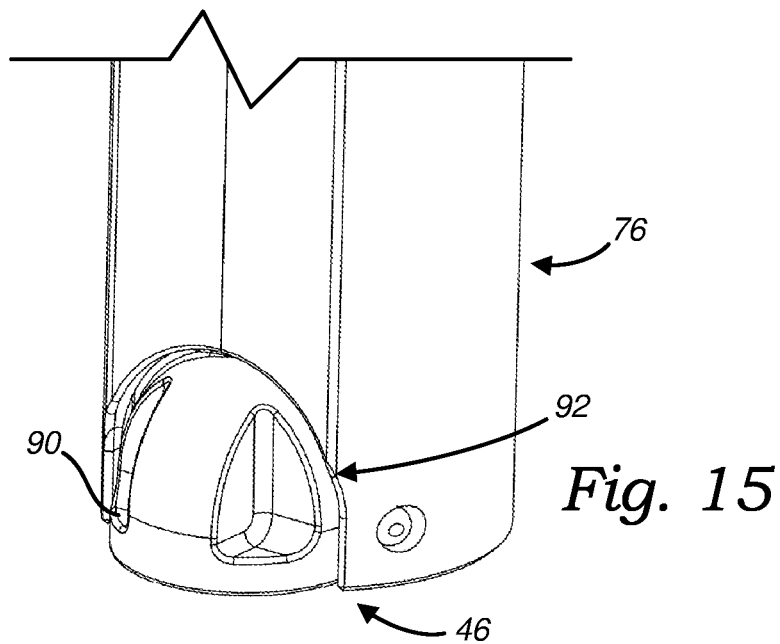
FIG. 15 is a partial perspective view of an exemplary collection portion of the apparatus in a closed position, in accordance with at least one embodiment.

In at least one such embodiment, as best illustrated in FIGS. 13-15, the collection scoop 46 is pivotally engaged with the first end 84 of the mixing portion 76. Thus, when the collection scoop 46 is in the open position (FIG. 13), the collection scoop 46 is pivoted away from the first end 84 of the mixing portion 76, allowing a volume of the substance 22 to be positioned within the collection scoop 46; and when the collection scoop 46 is subsequently moved into the closed position (FIG. 14), the collection scoop 46 is pivoted back into the first end 84 of the mixing portion 76, thereby moving the collected volume of the substance 22 from the collection scoop 46 through the inlet aperture 86 and into the mixing chamber 26. In at least one such embodiment, the first end 84 of the mixing portion 76 provides an O-ring, gasket or other type of sealing membrane positioned and configured for creating the fluid-tight seal between the collection scoop 46 and the first end 84 when the collection scoop 46 is in the closed position. However, in further embodiments, the apparatus 20 may utilize any other mechanisms or techniques, now known or later developed, capable of creating a fluid-tight seal between the collection scoop 46 and the first end 84 when the collection scoop 46 is in the closed position. In at least one embodiment, the collection scoop 46 provides a circumferential scoop wall 88 sized and configured for better preventing the collected volume of the substance 22 from spilling out of the collection scoop 46 as the collection scoop 46 is pivoted from the open position into the closed position. In at least one embodiment, as best illustrated in FIGS. 14 and 15, the collection scoop 46 further provides an access tab 90 positioned and configured for assisting in the movement of the collection scoop 46 from the closed position to the open position. In at least one such embodiment, the access tab 90 lies in substantially the same plane as the pivot point of the collection scoop 46; thus, applying force to the access tab 90 causes the access tab 90 (along with the rest of the collection scoop 46) to pivot from the closed position to the open position. Additionally, in at least one embodiment, as best illustrated in FIG. 15, the first end 84 of the mixing portion 76 provides a cutout 92 within the sidewall 80, positioned and configured for receiving the access tab 90 therewithin when the collection scoop 46 is in the open position, thereby allowing the access tab 90 to nest within the cutout 92 so as to be flush with the sidewall 80 of the mixing portion 76.

Figure 16:
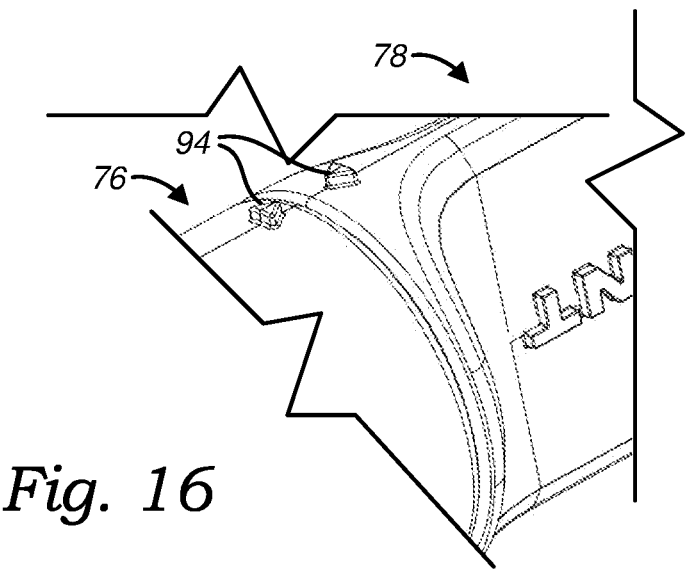
FIG. 16 is a partial perspective view of an exemplary status indicia of the apparatus, in accordance with at least one embodiment.
Figure 18:
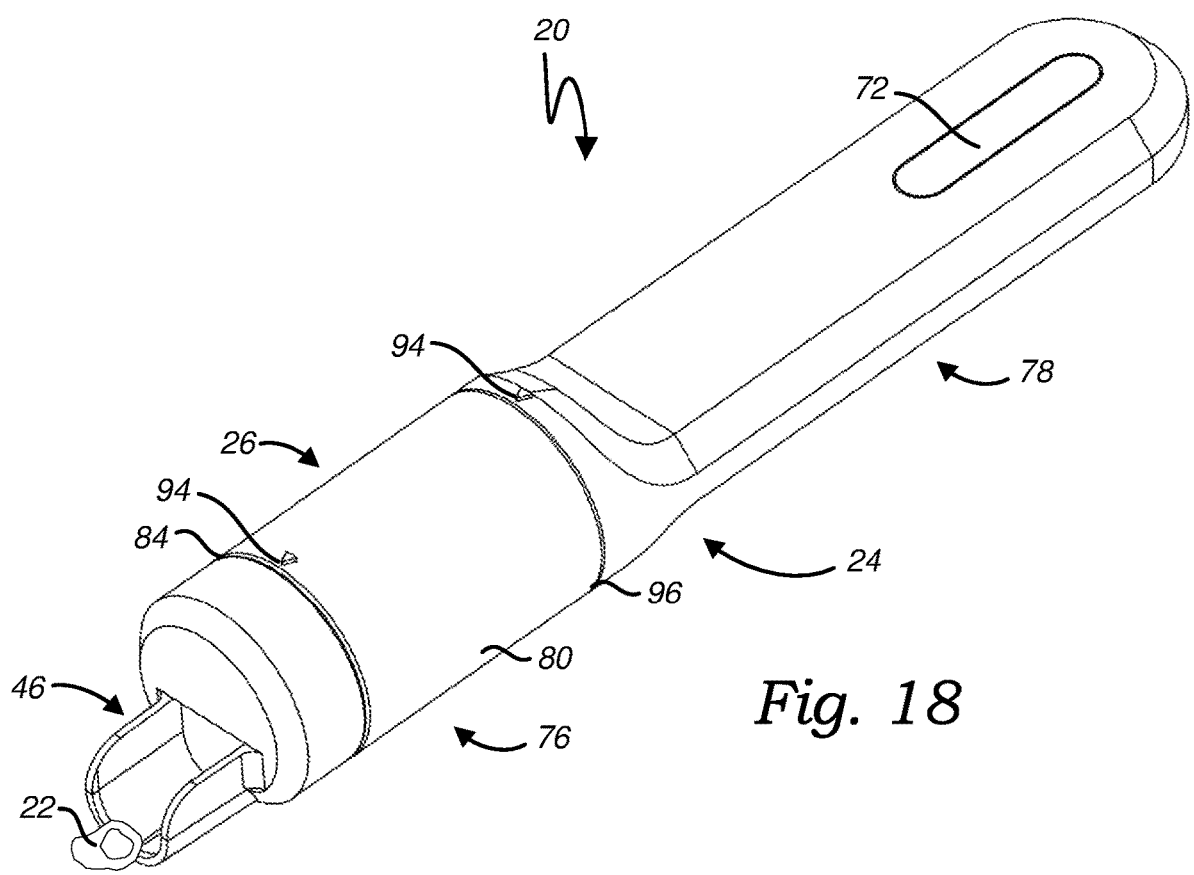
FIG. 18 is a perspective view of a further exemplary analyte detection apparatus, in accordance with at least one embodiment.

In at least one alternate embodiment, as best illustrated in FIG. 18, the collection scoop 46 is rotatably engaged with the first end 84 of the mixing portion 76, so as to be circumferentially rotatable (i.e., in a twisting motion) relative to the mixing portion 76. Thus, when the collection scoop 46 is in the open position, the collection scoop 46 is circumferentially rotated relative to the mixing portion 76 so as to be in fluid communication with the mixing chamber 26 via the inlet aperture 86, allowing a volume of the substance 22 to be collected by the collection scoop 46 and pass through the inlet aperture 86 and into the mixing chamber 26. When the collection scoop 46 is subsequently moved into the closed position, the collection scoop 46 is circumferentially rotated relative to the mixing portion 76 so as to obstruct the inlet aperture 86, thereby cutting off fluid communication between the collection scoop 46 and the mixing chamber 26. In at least one such embodiment, the inlet aperture 86 provides an O-ring, gasket or other type of sealing membrane positioned and configured for creating the fluid-tight seal between the collection scoop 46 and the inlet aperture 86 when the collection scoop 46 is in the closed position. However, in further embodiments, the apparatus 20 may utilize any other mechanisms or techniques, now known or later developed, capable of creating a fluid-tight seal between the collection scoop 46 and the inlet aperture 86 when the collection scoop 46 is in the closed position. Additionally, in at least one such embodiment, to prevent premature mixing of the substance 22 with the delivery fluid 56 in the mixing chamber 26, the substance 22 may be collected by the collection scoop 46 while the collection scoop 46 is in the closed position, thereby preventing the substance 22 from traveling into the mixing chamber 26 until the collection scoop 46 is subsequently moved into the open position. In at least one embodiment, as best illustrated in FIG. 16, one or both of the collection scoop 46 and mixing portion 76 provide an at least one position indicator 94 configured for visually indicating the current position of the collection scoop 46—i.e., open position or closed position. In at least one such embodiment, the collection scoop 46 and mixing portion 76 provide corresponding position indicators 94, such that when the collection scoop 46 is in the open position, the position indicators 94 are linearly aligned with one another. In further embodiments, the at least one position indicator 94 may take on any other sizes, shapes, dimensions, quantities and/or relative positions, now known or later developed, so long as the apparatus 20 is capable of substantially carrying out the functionality described herein. Similarly, in further embodiments, the collection scoop 46 may take on any other sizes, shapes, dimensions, configurations and/or relative positions, now known or later developed, so long as the apparatus 20 is capable of substantially carrying out the functionality described herein.

In at least one embodiment, as best illustrated in FIGS. 13 and 14, the testing portion 78 is rotatably engaged with an opposing second end 96 of the mixing portion 76, so as to be circumferentially rotatable (i.e., in a twisting motion) relative to the mixing portion 76, as discussed further below. Additionally, in at least one embodiment, the testing portion 78 defines an internal testing chamber 28 sized and configured for containing a test medium 54 therewithin, the test medium 54 configured for visually indicating the presence or absence of the at least one target analyte within the substance 22. In at least one embodiment, the test medium 54 is a lateral flow test strip 58. In at least one alternate embodiment, the test medium 54 is a volume of an appropriate reagent configured to react to the at least one target analyte. In still further embodiments, the test medium 54 may be any other type of test medium 54, now known or later developed, capable of visually indicating the presence or absence of the at least one target analyte within the substance 22.

In at least one embodiment, the second end 96 of the mixing portion 76 provides an outlet aperture 98 in fluid communication with the mixing chamber 26, while the testing portion 78 provides a testing aperture 62 in fluid communication with the testing chamber 28. In at least one embodiment, the testing portion 78 is configured for moving between one of an open position—wherein the testing portion 78 is circumferentially rotated relative to the mixing portion 76 so as to place the outlet aperture 98 of the mixing portion 76 in fluid communication with the testing aperture 62 of the testing portion 78, allowing a volume of the substance 22 (along with the delivery fluid 56, where applicable) to travel through each of the outlet aperture 98 and testing aperture 62 and into the testing chamber 28—and a closed position—wherein the testing portion 78 is circumferentially rotated relative to the mixing portion 76 so as to obstruct the outlet aperture 98, thereby cutting off fluid communication and creating a fluid-tight seal between the mixing chamber 26 and the testing chamber 28. In at least one such embodiment, one or both of the outlet aperture 98 and testing aperture 62 provides an O-ring, gasket or other type of sealing membrane positioned and configured for creating the fluid-tight seal between the mixing chamber 26 and the testing chamber 28 when the testing portion 78 is in the closed position. However, in further embodiments, the apparatus 20 may utilize any other mechanisms or techniques, now known or later developed, capable of creating a fluid-tight seal between the mixing chamber 26 and the testing chamber 28 when the testing portion 78 is in the closed position.

In at least one embodiment, the test medium 54 is positioned substantially adjacent to the testing aperture 62 so as to come into contact with the substance 22 (along with the delivery fluid 56, where applicable) as it passes through the testing aperture 62 and enters the testing chamber 28. Thus, where the test medium 54 is a test strip 58, a sample pad of the test strip 58 is positioned substantially adjacent to the testing aperture 62. In at least one embodiment, where the testing portion 78 is constructed out of an opaque material, the testing portion 78 further provides an at least one transparent or translucent result window 72 positioned and configured for providing visual access into the testing chamber 28 during use of the apparatus 20, in order to view the visual indication of the presence or absence of the at least one target analyte within the substance 22 as provided by the test medium 54. In that regard, it should be noted that the at least one result window 72 may take on any other sizes, shapes, dimensions, configurations and/or relative positions, now known or later developed—dependent at least in part on the test medium 54—so long as the apparatus 20 is capable of substantially carrying out the functionality described herein. Thus, in at least one embodiment, where the test medium 54 is a test strip 58, the at least one result window 72 is substantially aligned with a detection zone of the test strip 58 (i.e., the portion of the test strip 58 containing each of a test line and a control line). Additionally, in at least one embodiment, as best illustrated in FIG. 14, where the test medium 54 is a test strip 58 or other type of test medium 54 where the result portion of the test medium 54 (such as the detection zone in the case of a test strip 58) must remain substantially dry, the testing chamber 28 defines a separate result chamber 100 that is substantially sealed off from a remaining portion of the testing chamber 28, within which the result portion of the test medium 54 is positioned, thereby preventing the substance 22 (along with the delivery fluid 56, where applicable) from flowing into the result chamber 100 and saturating the result portion of the test medium 54.

In at least one embodiment, one or both of the testing portion 78 and mixing portion 76 provide an at least one position indicator 94 configured for visually indicating the current position of the testing portion 78—i.e., open position or closed position. In at least one such embodiment, the testing portion 78 and mixing portion 76 provide corresponding position indicators 94, such that when the testing portion 78 is in the open position, the position indicators 94 are linearly aligned with one another. In further embodiments, the at least one position indicator 94 may take on any other sizes, shapes, dimensions, quantities and/or relative positions, now known or later developed, so long as the apparatus 20 is capable of substantially carrying out the functionality described herein.

Figure 17:
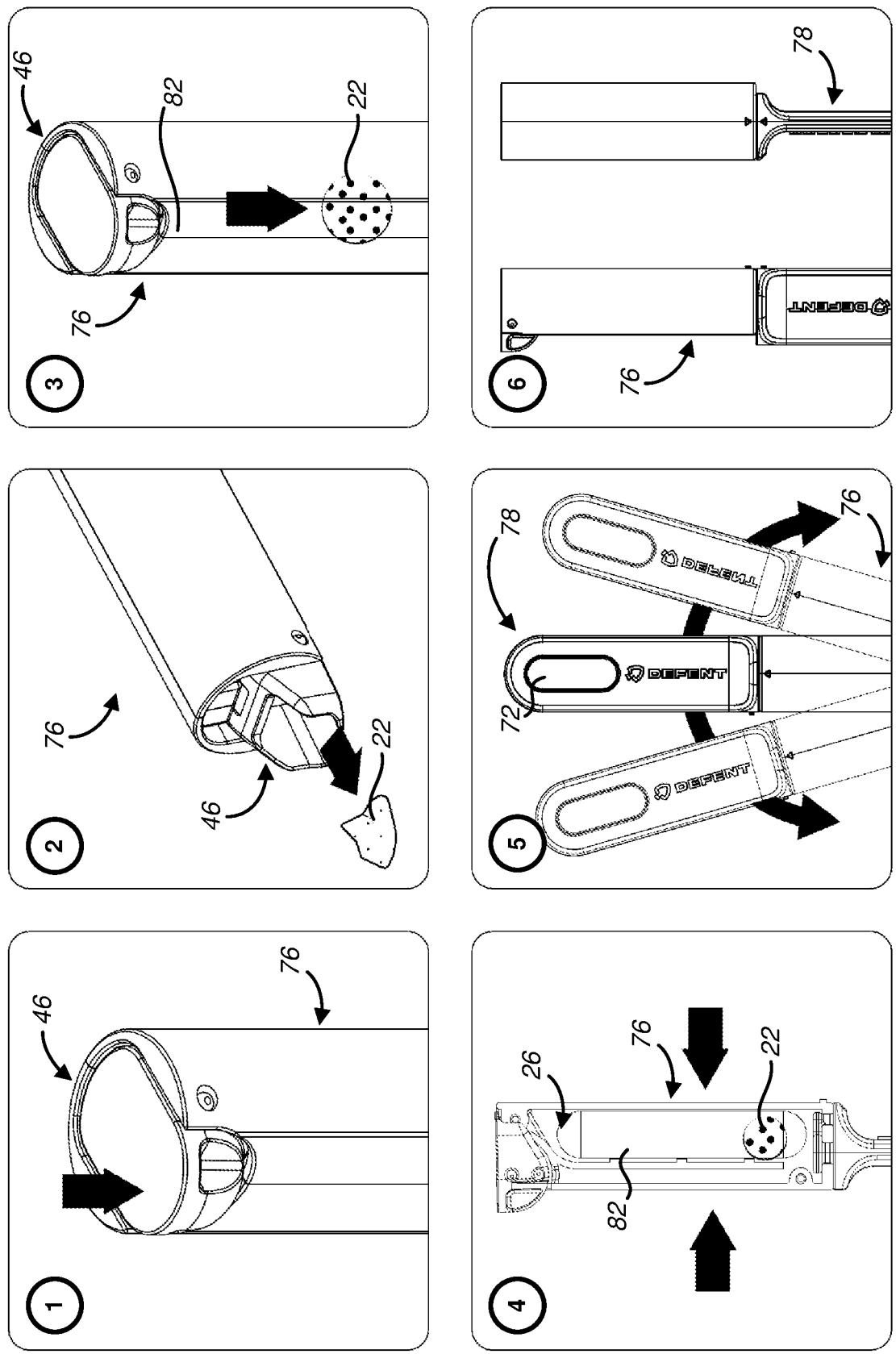
FIG. 17 is a diagrammatic sequence illustrating an exemplary method for testing a substance for the presence or absence of an at least one target analyte using an exemplary analyte detection apparatus, in accordance with at least one embodiment.
Figure 19:
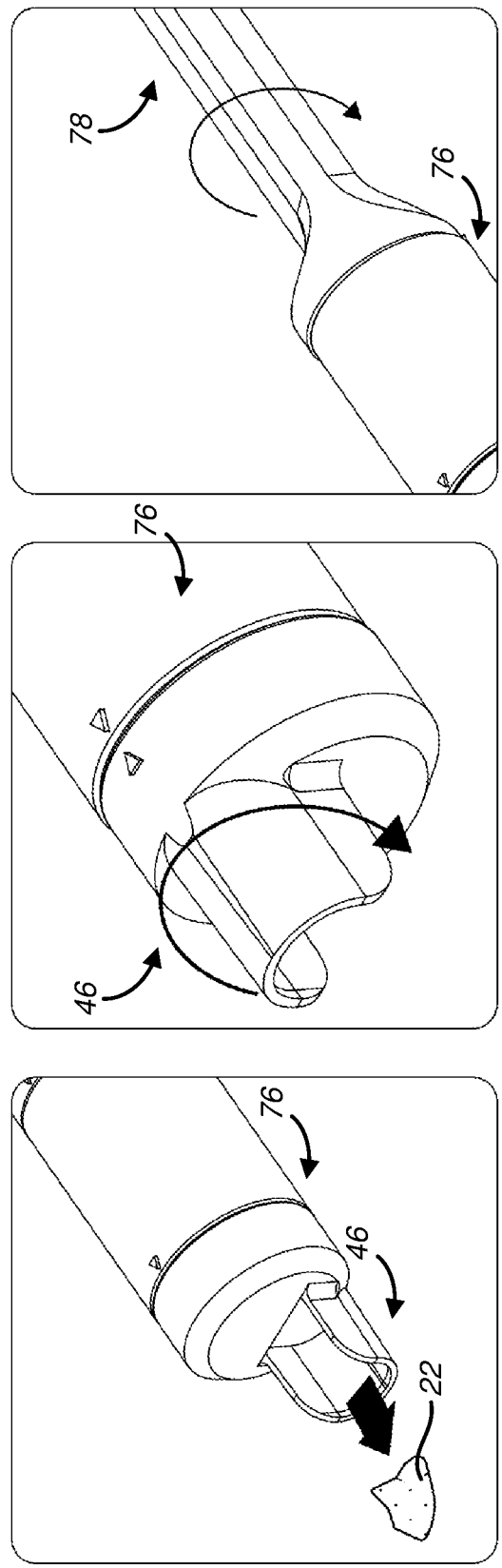
FIG. 19 is a diagrammatic sequence illustrating an exemplary method for testing a substance for the presence or absence of an at least one target analyte using an exemplary analyte detection apparatus, in accordance with at least one embodiment.
Figure 20:
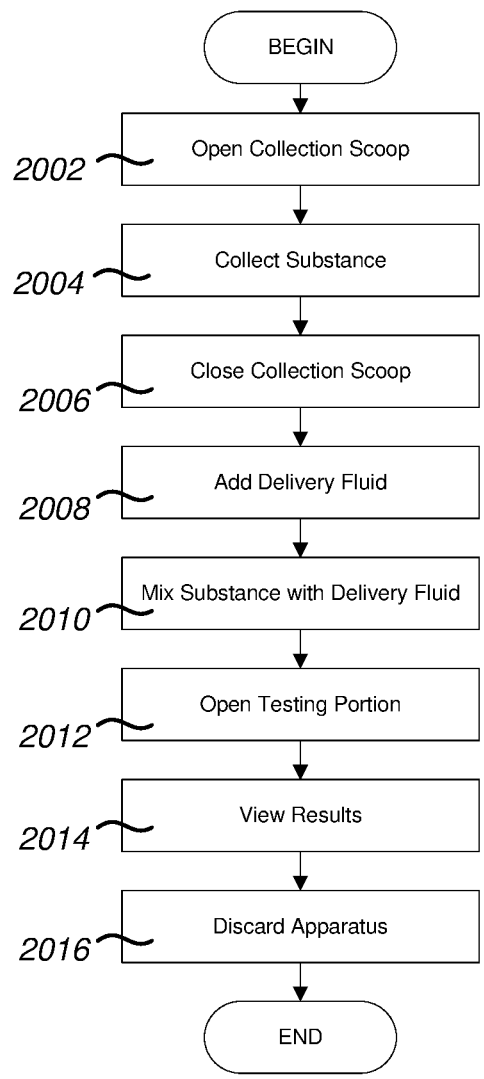
FIG. 20 is a flow diagram of a further exemplary method for testing a substance for the presence or absence of an at least one target analyte, in accordance with at least one embodiment.

In at least one embodiment, as illustrated in FIGS. 17 and 19 along with the flow diagram of FIG. 20, during use of the apparatus 20, with the testing portion 78 in the closed position, the collection scoop 46 is moved into the open position (2002), and an appropriate volume of the substance 22 is collected and inserted into the mixing chamber 26 (2004). The collection scoop 46 is moved into the closed position (2006) and the substance 22 is then mixed with the delivery fluid 56 (where applicable) (2008). In at least one such embodiment, where the delivery fluid 56 is contained within a breakable fluid capsule 82 positioned within the mixing chamber 26, the fluid capsule 82 is broken. In at least one embodiment, where delivery fluid 56 is present, the apparatus 20 is shaken so as to mix the substance 22 with the delivery fluid 56 (2010)—and where the substance 22 is solid, the substance 22 is allowed to dissolve in the delivery fluid 56. The testing portion 78 is then moved into the open position (2012), allowing an appropriate volume of the substance 22 (along with the delivery fluid 56, where applicable) to come into contact with the test medium 54. The results of the test are then viewable via the result window 72 (2014). In at least one embodiment, the apparatus 20 is designed for one-time use, such that the apparatus 20 may be discarded after the results of the test are viewed (2016). Thus, in at least one embodiment, the apparatus 20 is a small, self-contained, user-friendly device capable of quickly and easily testing the substance 22 for the presence or absence of one or more target analytes—both at work or at home, as well as while on the go.

Aspects of the present specification may also be described as the following embodiments:

1. An analyte detection apparatus configured for testing a substance for the presence or absence of an at least one target analyte, the apparatus comprising: a housing; a mixing chamber positioned within the housing, the mixing chamber sized and configured for temporarily storing a volume of the substance and a volume of a delivery fluid; a testing chamber positioned within the housing and in selective fluid communication with the mixing chamber, the testing chamber sized and configured for containing a test medium therewithin, the test medium configured for visually indicating the presence or absence of the at least one target analyte within the substance; a scoop storage chamber positioned within the housing; a first end of the housing providing a first chamber opening in fluid communication with the scoop storage chamber and a second chamber opening in fluid communication with the mixing chamber, the first and second chamber openings providing access to the scoop storage chamber and mixing chamber, respectively; an end cap sized and configured for removable engagement with the first end of the housing; an elongate collection scoop extending substantially perpendicularly from an engagement end of the end cap and providing an at least one substance receptacle sized and configured for receiving an appropriate volume of the substance; the end cap configured for removable engagement with the first end of the housing in each of a first cap orientation—wherein the collection scoop extends through the first chamber opening so as to be positioned within the scoop storage chamber—and a second cap orientation—wherein the collection scoop extends through the second chamber opening so as to be positioned within the mixing chamber; the mixing chamber providing a mixing aperture; the testing chamber providing a testing aperture in selective fluid communication with the mixing aperture; a mixing valve positioned inline between the mixing aperture and the testing aperture within the housing, the mixing valve rotatably engaged with the housing and configured for selectively rotating between one of an open position—wherein the mixing valve is circumferentially rotated relative to the housing so as to place the mixing aperture in fluid communication with the testing aperture, allowing an appropriate volume of the substance to travel through each of the mixing aperture and testing aperture and into the testing chamber—and a closed position—wherein the mixing valve is circumferentially rotated relative to the housing so as to obstruct fluid communication between the mixing aperture and testing aperture; and the housing and testing chamber cooperating to provide an at least one result window positioned and configured for providing visual access into the testing chamber during use of the apparatus; whereby, during use of the apparatus, with the end cap engaged with the first end of the housing in the first cap orientation, the end cap is disengaged from the first end of the housing, an appropriate volume of the substance is collected via the at least one substance receptacle of the collection scoop, the end cap is re-engaged with the first end of the housing in the second cap orientation, thereby introducing the volume of substance from the collection scoop into the mixing chamber, the substance is mixed with the delivery fluid within the mixing chamber, and the mixing valve is rotated into the open position, allowing an appropriate volume of the substance to travel into the testing chamber and come into contact with the test medium, with a resulting visual indication from the test medium being viewable via the at least one result window.

2. The analyte detection apparatus according to embodiment 1, wherein a sidewall of the housing provides a relatively planar surface positioned and configured for preventing the housing from unintentionally rolling when placed on an uneven surface.

3. The analyte detection apparatus according to embodiments 1-2, wherein: the mixing chamber is positioned substantially adjacent to the scoop storage chamber within the housing; and the first chamber opening is positioned substantially adjacent to the second chamber opening.

4. The analyte detection apparatus according to embodiments 1-3, wherein: the mixing chamber and scoop storage chamber are positioned in a substantially side-by-side arrangement within the housing; and the first chamber opening and second chamber opening are positioned in a substantially side-by-side arrangement.

5. The analyte detection apparatus according to embodiments 1-4, wherein an engagement end of the end cap is frictionally engageable with the first end of the housing, thereby providing a fluid-tight and pressurized seal between the engagement end of the end cap and one or both of the first and second chamber openings.

6. The analyte detection apparatus according to embodiments 1-5, wherein the first end of the housing provides an O-ring, gasket or other type of sealing membrane positioned and configured for creating the fluid-tight seal between the engagement end of the end cap and one or both of the first and second chamber openings.

7. The analyte detection apparatus according to embodiments 1-6, wherein the at least one substance receptacle is positioned proximal to a terminal end of the collection scoop.

8. The analyte detection apparatus according to embodiments 1-7, wherein the end cap further provides a relatively flat grip portion positioned substantially opposite to the engagement end, the grip portion sized and configured for facilitating the handling and manual operation of the end cap, along with the apparatus generally, during use.

9. The analyte detection apparatus according to embodiments 1-8, wherein the mixing chamber is further sized and configured for receiving the collection scoop therewithin when the end cap is engaged with the first end of the housing in the second cap orientation.

10. The analyte detection apparatus according to embodiments 1-9, wherein the scoop storage container is sized and configured for receiving the collection scoop therewithin when the end cap is engaged with the first end of the housing in the first cap orientation.

11. The analyte detection apparatus according to embodiments 1-10, wherein the scoop storage chamber is sized to approximate the dimensions of the collection scoop.

12. The analyte detection apparatus according to embodiments 1-11, wherein the delivery fluid is temporarily contained within a breakable fluid capsule positioned within the mixing chamber.

13. The analyte detection apparatus according to embodiments 1-12, wherein a sidewall of the housing is constructed out of a relatively resilient material, thereby allowing the housing to be temporarily radially collapsed inwardly in order to break the fluid capsule and release the delivery fluid into the mixing chamber.

14. The analyte detection apparatus according to embodiments 1-13, wherein a sidewall of the housing, along with at least a portion of the mixing chamber, is transparent or translucent, thereby providing visual access into the mixing chamber during use of the apparatus.

15. The analyte detection apparatus according to embodiments 1-14, wherein the test medium is a lateral flow test strip.

16. The analyte detection apparatus according to embodiments 1-15, wherein a sample pad of the test strip is positioned substantially adjacent to the testing aperture.

17. The analyte detection apparatus according to embodiments 1-16, wherein the at least one result window is substantially aligned with a detection zone of the test strip.

18. The analyte detection apparatus according to embodiments 1-17, wherein: the testing chamber defines a separate result chamber that is substantially sealed off from a remaining portion of the testing chamber along with the testing aperture; and a detection zone of the test strip is positioned within the result chamber.

19. The analyte detection apparatus according to embodiments 1-18, wherein the test medium is a volume of an appropriate reagent configured to react to the at least one target analyte.

20. The analyte detection apparatus according to embodiments 1-19, wherein the test medium is positioned substantially adjacent to the testing aperture so as to come into contact with the substance as the volume of the substance enters the testing chamber when the mixing valve is in the open position.

21. The analyte detection apparatus according to embodiments 1-20, wherein one or both of the mixing aperture and testing aperture provides an O-ring, gasket or other type of sealing membrane positioned and configured for creating a fluid-tight seal between the mixing chamber and the testing chamber when the mixing valve is in the closed position.

22. The analyte detection apparatus according to embodiments 1-21, further comprising a valve knob rotatably engaged with the housing and in mechanical communication with the mixing valve, the valve knob configured for enabling the mixing valve to be manually rotated between the open position and closed position during use of the apparatus.

23. The analyte detection apparatus according to embodiments 1-22, wherein the valve knob is rotatably engaged with an opposing second end of the housing.

24. The analyte detection apparatus according to embodiments 1-23, wherein one or both of the valve knob and housing provide an at least one position indicator configured for visually indicating the current position of the mixing valve.

25. The analyte detection apparatus according to embodiments 1-24, wherein: the valve knob and housing provide corresponding position indicators; whereby, when the mixing valve is in the open position, the position indicators on the valve knob and housing are linearly aligned with one another.

26. The analyte detection apparatus according to embodiments 1-25, wherein the valve knob is shaped for visually indicating the current position of the mixing valve.

27. An analyte detection apparatus configured for testing a substance for the presence or absence of an at least one target analyte, the apparatus comprising: a housing; a mixing chamber positioned within the housing, the mixing chamber sized and configured for temporarily storing a volume of the substance and a volume of a delivery fluid; a testing chamber positioned within the housing and in selective fluid communication with the mixing chamber, the testing chamber sized and configured for containing a test medium therewithin, the test medium configured for visually indicating the presence or absence of the at least one target analyte within the substance; a scoop storage chamber positioned within the housing; a first end of the housing providing a first chamber opening in fluid communication with the scoop storage chamber and a second chamber opening in fluid communication with the mixing chamber, the first and second chamber openings providing access to the scoop storage chamber and mixing chamber, respectively; an end cap sized and configured for removable engagement with the first end of the housing; an elongate collection scoop extending substantially perpendicularly from an engagement end of the end cap and providing an at least one substance receptacle sized and configured for receiving an appropriate volume of the substance; the end cap configured for removable engagement with the first end of the housing in each of a first cap orientation—wherein the collection scoop extends through the first chamber opening so as to be positioned within the scoop storage chamber—and a second cap orientation—wherein the collection scoop extends through the second chamber opening so as to be positioned within the mixing chamber; the mixing chamber providing a mixing aperture; the testing chamber providing a testing aperture in selective fluid communication with the mixing aperture; a mixing valve positioned inline between the mixing aperture and the testing aperture within the housing, the mixing valve rotatably engaged with the housing and configured for selectively rotating between one of an open position—wherein the mixing valve is circumferentially rotated relative to the housing so as to place the mixing aperture in fluid communication with the testing aperture, allowing an appropriate volume of the substance to travel through each of the mixing aperture and testing aperture and into the testing chamber—and a closed position—wherein the mixing valve is circumferentially rotated relative to the housing so as to obstruct fluid communication between the mixing aperture and testing aperture; a valve knob rotatably engaged with the housing and in mechanical communication with the mixing valve, the valve knob configured for enabling the mixing valve to be manually rotated between the open position and closed position during use of the apparatus; and the housing and testing chamber cooperating to provide an at least one result window positioned and configured for providing visual access into the testing chamber during use of the apparatus; whereby, during use of the apparatus, with the end cap engaged with the first end of the housing in the first cap orientation, the end cap is disengaged from the first end of the housing, an appropriate volume of the substance is collected via the at least one substance receptacle of the collection scoop, the end cap is re-engaged with the first end of the housing in the second cap orientation, thereby introducing the volume of substance from the collection scoop into the mixing chamber, the substance is mixed with the delivery fluid within the mixing chamber, and the mixing valve is rotated into the open position, allowing an appropriate volume of the substance to travel into the testing chamber and come into contact with the test medium, with a resulting visual indication from the test medium being viewable via the at least one result window.

28. An analyte detection apparatus configured for testing a substance for the presence or absence of an at least one target analyte, the apparatus comprising: a housing; a mixing chamber positioned within the housing, the mixing chamber sized and configured for temporarily storing a volume of the substance and a volume of a delivery fluid; a testing chamber positioned within the housing and in selective fluid communication with the mixing chamber, the testing chamber sized and configured for containing a test medium therewithin, the test medium configured for visually indicating the presence or absence of the at least one target analyte within the substance; a first end of the housing providing a chamber opening in fluid communication with the mixing chamber for providing access thereto; an end cap sized and configured for removable frictional engagement with the first end of the housing, thereby providing a fluid-tight and pressurized seal between an engagement end of the end cap and the chamber opening; an elongate collection scoop extending substantially perpendicularly from the engagement end of the end cap and providing an at least one substance receptacle sized and configured for receiving an appropriate volume of the substance; the mixing chamber providing a mixing aperture; the testing chamber providing a testing aperture in selective fluid communication with the mixing aperture; a mixing valve positioned inline between the mixing aperture and the testing aperture within the housing, the mixing valve rotatably engaged with the housing and configured for selectively rotating between one of an open position—wherein the mixing valve is circumferentially rotated relative to the housing so as to place the mixing aperture in fluid communication with the testing aperture, allowing an appropriate volume of the substance to travel through each of the mixing aperture and testing aperture and into the testing chamber—and a closed position—wherein the mixing valve is circumferentially rotated relative to the housing so as to obstruct fluid communication between the mixing aperture and testing aperture; and the housing and testing chamber cooperating to provide an at least one result window positioned and configured for providing visual access into the testing chamber during use of the apparatus; whereby, during use of the apparatus, with the end cap engaged with the first end of the housing, the end cap is disengaged from the first end of the housing, an appropriate volume of the substance is collected via the at least one substance receptacle of the collection scoop, the end cap is re-engaged with the first end of the housing, thereby introducing the volume of substance from the collection scoop into the mixing chamber, the substance is mixed with the delivery fluid within the mixing chamber, and the mixing valve is rotated into the open position, allowing an appropriate volume of the substance to travel into the testing chamber and come into contact with the test medium, with a resulting visual indication from the test medium being viewable via the at least one result window.

29. An analyte detection apparatus configured for testing a substance for the presence or absence of an at least one target analyte, the apparatus comprising: a housing providing a mixing portion and a testing portion; the mixing portion defining an internal mixing chamber sized and configured for temporarily storing a volume of the substance and a volume of a delivery fluid; a first end of the mixing portion providing an inlet aperture in fluid communication with the mixing chamber, the inlet aperture sized and configured for allowing the volume of the substance to pass therethrough and into the mixing chamber; a collection scoop positioned within the first end of the mixing portion and configured for moving between one of an open position—wherein the collection scoop is oriented so as to assist in the collection of the volume of the substance therewithin, and subsequently move the collected volume of the substance through the inlet aperture and into the mixing chamber—and a closed position—wherein the collection scoop is oriented so as to create a fluid-tight seal with the first end of the mixing portion, thereby preventing any of the volume of the substance or delivery fluid from unintentionally escaping through the inlet aperture; an opposing second end of the mixing portion providing an outlet aperture in fluid communication with the mixing chamber; the testing portion rotatably engaged with the second end of the mixing portion, so as to be circumferentially rotatable relative to the mixing portion; the testing portion defining an internal testing chamber sized and configured for containing a test medium therewithin, the test medium configured for visually indicating the presence or absence of the at least one target analyte within the substance; the testing portion providing a testing aperture in fluid communication with the testing chamber; the testing chamber configured for moving between one of an open position—wherein the testing portion is circumferentially rotated relative to the mixing portion so as to place the outlet aperture of the mixing portion in fluid communication with the testing aperture of the testing portion, allowing an appropriate volume of the substance to travel through each of the outlet aperture and testing aperture and into the testing chamber—and a closed position—wherein the testing portion is circumferentially rotated relative to the mixing portion so as to obstruct the outlet aperture, thereby cutting off fluid communication and creating a fluid-tight seal between the mixing chamber and the testing chamber; and the testing portion providing an at least one result window positioned and configured for providing visual access into the testing chamber during use of the apparatus; whereby, during use of the apparatus, with the testing portion in the closed position, the collection scoop is moved into the open position, the volume of the substance is collected and inserted into the mixing chamber, the collection scoop is moved into the closed position, the substance is mixed with the delivery fluid, and the testing portion is moved into the open position, allowing an appropriate volume of the substance to travel into the testing chamber and come into contact with the test medium, with a resulting visual indication from the test medium being viewable via the at least one result window.

30. The analyte detection apparatus according to embodiment 29, wherein the volume of delivery fluid is contained within a breakable fluid capsule positioned within the mixing chamber.

31. The analyte detection apparatus according to embodiments 29-30, wherein a sidewall of the mixing portion is constructed out of a relatively resilient material, thereby allowing the mixing portion to be temporarily radially collapsed inwardly in order to break the fluid capsule and release the delivery fluid into the mixing chamber.

32. The analyte detection apparatus according to embodiments 29-31, wherein a sidewall of the mixing portion is transparent or translucent, thereby providing visual access into the mixing chamber during use of the apparatus.

33. The analyte detection apparatus according to embodiments 29-32, wherein: the collection scoop is pivotally engaged with the first end of the mixing portion; whereby, when the collection scoop is in the open position, the collection scoop is pivoted away from the first end of the mixing portion, allowing the volume of the collected substance to be positioned within the collection scoop; and whereby, when the collection scoop is subsequently moved into the closed position, the collection scoop is pivoted back into the first end of the mixing portion, thereby moving the collected volume of the substance from the collection scoop through the inlet aperture and into the mixing chamber.

34. The analyte detection apparatus according to embodiments 29-33, wherein the first end of the mixing portion provides an O-ring, gasket or other type of sealing membrane positioned and configured for creating the fluid-tight seal between the collection scoop and the first end when the collection scoop is in the closed position.

35. The analyte detection apparatus according to embodiments 29-34, wherein the collection scoop provides a circumferential scoop wall sized and configured for better preventing the collected volume of the substance from spilling out of the collection scoop as the collection scoop is pivoted from the open position into the closed position.

36. The analyte detection apparatus according to embodiments 29-35, wherein the collection scoop provides an access tab positioned and configured for assisting in the movement of the collection scoop from the closed position to the open position.

37. The analyte detection apparatus according to embodiments 29-36, wherein: the collection scoop is rotatably engaged with the first end of the mixing portion, so as to be circumferentially rotatable relative to the mixing portion; whereby, when the collection scoop is in the open position, the collection scoop is circumferentially rotated relative to the mixing portion so as to be in fluid communication with the mixing chamber via the inlet aperture, allowing the volume of the substance to be collected by the collection scoop, pass through the inlet aperture and into the mixing chamber; and whereby, when the collection scoop is subsequently moved into the closed position, the collection scoop is circumferentially rotated relative to the mixing portion so as to obstruct the inlet aperture, thereby cutting off fluid communication between the collection scoop and the mixing chamber.

38. The analyte detection apparatus according to embodiments 29-37, wherein the inlet aperture of the mixing portion provides an O-ring, gasket or other type of sealing membrane positioned and configured for creating a fluid-tight seal between the collection scoop and the inlet aperture when the collection scoop is in the closed position.

39. The analyte detection apparatus according to embodiments 29-38, wherein one or both of the collection scoop and mixing portion provide an at least one position indicator configured for visually indicating a current position of the collection scoop.

40. The analyte detection apparatus according to embodiments 29-39, wherein: the collection scoop and mixing portion provide corresponding position indicators; whereby, when the collection scoop is in the open position, the position indicators are linearly aligned with one another.

41. The analyte detection apparatus according to embodiments 29-40, wherein the test medium is a lateral flow test strip.

42. The analyte detection apparatus according to embodiments 29-41, wherein a sample pad of the test strip is positioned substantially adjacent to the testing aperture.

43. The analyte detection apparatus according to embodiments 29-42, wherein: the testing chamber defines a separate result chamber that is substantially sealed off from a remaining portion of the testing chamber along with the testing aperture; and a result portion of the test strip is positioned within the result chamber.

44. The analyte detection apparatus according to embodiments 29-43, wherein the test medium is a volume of an appropriate reagent configured to react to the at least one target analyte.

45. The analyte detection apparatus according to embodiments 29-44, wherein one or both of the outlet aperture and testing aperture provides an O-ring, gasket or other type of sealing membrane positioned and configured for creating a fluid-tight seal between the mixing chamber and the testing chamber when the testing portion is in the closed position.

46. The analyte detection apparatus according to embodiments 29-45, wherein the test medium is positioned substantially adjacent to the testing aperture so as to come into contact with the substance as the volume of the substance enters the testing chamber when the testing portion is in the open position.

47. The analyte detection apparatus according to embodiments 29-46, wherein one or both of the testing portion and mixing portion provide an at least one position indicator configured for visually indicating a current position of the testing portion.

48. The analyte detection apparatus according to embodiments 29-47, wherein: the testing portion and mixing portion provide corresponding position indicators; whereby, when the testing portion is in the open position, the position indicators are linearly aligned with one another.

49. An analyte detection apparatus configured for testing a substance for the presence or absence of an at least one target analyte, the apparatus comprising: a housing providing a mixing portion and a testing portion; the mixing portion defining an internal mixing chamber sized and configured for temporarily storing a volume of the substance and a volume of a delivery fluid; a first end of the mixing portion providing an inlet aperture in fluid communication with the mixing chamber, the inlet aperture sized and configured for allowing the volume of the substance to pass therethrough and into the mixing chamber; a collection scoop pivotally engaged with the first end of the mixing portion and configured for moving between one of an open position—wherein the collection scoop is pivoted away from the first end of the mixing portion, allowing the volume of the substance to be collected and positioned within the collection scoop—and a closed position—wherein the collection scoop is pivoted back into the first end of the mixing portion, thereby moving the collected volume of the substance from the collection scoop through the inlet aperture and into the mixing chamber while also creating a fluid-tight seal with the first end of the mixing portion; an opposing second end of the mixing portion providing an outlet aperture in fluid communication with the mixing chamber; the testing portion rotatably engaged with the second end of the mixing portion, so as to be circumferentially rotatable relative to the mixing portion; the testing portion defining an internal testing chamber sized and configured for containing a test medium therewithin, the test medium configured for visually indicating the presence or absence of the at least one target analyte within the substance; the testing portion providing a testing aperture in fluid communication with the testing chamber; the testing chamber configured for moving between one of an open position—wherein the testing portion is circumferentially rotated relative to the mixing portion so as to place the outlet aperture of the mixing portion in fluid communication with the testing aperture of the testing portion, allowing an appropriate volume of the substance to travel through each of the outlet aperture and testing aperture and into the testing chamber—and a closed position—wherein the testing portion is circumferentially rotated relative to the mixing portion so as to obstruct the outlet aperture, thereby cutting off fluid communication and creating a fluid-tight seal between the mixing chamber and the testing chamber; and the testing portion providing an at least one result window positioned and configured for providing visual access into the testing chamber during use of the apparatus; whereby, during use of the apparatus, with the testing portion in the closed position, the collection scoop is moved into the open position, the volume of the substance is collected and inserted into the mixing chamber, the collection scoop is moved into the closed position, the substance is mixed with the delivery fluid, and the testing portion is moved into the open position, allowing an appropriate volume of the substance to travel into the testing chamber and come into contact with the test medium, with a resulting visual indication from the test medium being viewable via the at least one result window.

50. An analyte detection apparatus configured for testing a substance for the presence or absence of an at least one target analyte, the apparatus comprising: a housing providing a mixing portion and a testing portion; the mixing portion defining an internal mixing chamber sized and configured for temporarily storing a volume of the substance and a volume of a delivery fluid; a first end of the mixing portion providing an inlet aperture in fluid communication with the mixing chamber, the inlet aperture sized and configured for allowing the volume of the substance to pass therethrough and into the mixing chamber; a collection scoop rotatably engaged with the first end of the mixing portion, so as to be circumferentially rotatable relative to the mixing portion, the collection scoop configured for moving between one of an open position—wherein the collection scoop is circumferentially rotated relative to the mixing portion so as to be in fluid communication with the mixing chamber via the inlet aperture, allowing the volume of the substance to be collected by the collection scoop, pass through the inlet aperture and into the mixing chamber—and a closed position—wherein the collection scoop is circumferentially rotated relative to the mixing portion so as to obstruct the inlet aperture, thereby cutting off fluid communication between the collection scoop and the mixing chamber; an opposing second end of the mixing portion providing an outlet aperture in fluid communication with the mixing chamber; the testing portion rotatably engaged with the second end of the mixing portion, so as to be circumferentially rotatable relative to the mixing portion; the testing portion defining an internal testing chamber sized and configured for containing a test medium therewithin, the test medium configured for visually indicating the presence or absence of the at least one target analyte within the substance; the testing portion providing a testing aperture in fluid communication with the testing chamber; the testing chamber configured for moving between one of an open position—wherein the testing portion is circumferentially rotated relative to the mixing portion so as to place the outlet aperture of the mixing portion in fluid communication with the testing aperture of the testing portion, allowing an appropriate volume of the substance to travel through each of the outlet aperture and testing aperture and into the testing chamber—and a closed position—wherein the testing portion is circumferentially rotated relative to the mixing portion so as to obstruct the outlet aperture, thereby cutting off fluid communication and creating a fluid-tight seal between the mixing chamber and the testing chamber; and the testing portion providing an at least one result window positioned and configured for providing visual access into the testing chamber during use of the apparatus; whereby, during use of the apparatus, with the testing portion in the closed position, the collection scoop is moved into the open position, the volume of the substance is collected and inserted into the mixing chamber, the collection scoop is moved into the closed position, the substance is mixed with the delivery fluid, and the testing portion is moved into the open position, allowing an appropriate volume of the substance to travel into the testing chamber and come into contact with the test medium, with a resulting visual indication from the test medium being viewable via the at least one result window.

In closing, regarding the exemplary embodiments of the present invention as shown and described herein, it will be appreciated that an analyte detection apparatus is disclosed and configured for testing a substance for the presence or absence of an at least one target analyte. Because the principles of the invention may be practiced in a number of configurations beyond those shown and described, it is to be understood that the invention is not in any way limited by the exemplary embodiments, but is generally directed to an analyte detection apparatus and is able to take numerous forms to do so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the terms "about" and "approximately." As used herein, the terms "about" and "approximately" mean that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein. Similarly, as used herein, unless indicated to the contrary, the term "substantially" is a term of degree intended to indicate an approximation of the characteristic, item, quantity, parameter, property, or term so qualified, encompassing a range that can be understood and construed by those of ordinary skill in the art, or at least encompassing a range of plus or minus ten percent above and below the value of the stated characteristic, item, quantity, parameter, property, or term.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators-such as "first," "second," "third," etc.— for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (along with equivalent open-ended transitional phrases thereof such as "including," "containing" and "having") encompasses all the expressly recited elements, limitations, steps and/or features alone or in combination with un-recited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amendment for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim, whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (along with equivalent open-ended transitional phrases thereof) includes within its meaning, as a limiting case, claimed subject matter specified by the closed-ended transitional phrases "consisting of" or "consisting essentially of." As such, embodiments described herein or so claimed with the phrase "comprising" are expressly or inherently unambiguously described, enabled and supported herein for the phrases "consisting essentially of" and "consisting of."

Any claims intended to be treated under 35 U.S.C. § 112(f) will begin with the words "means for," but use of the term "for" in any other context is not intended to invoke treatment under 35 U.S.C. § 112(f). Accordingly, Applicant reserves the right to pursue additional claims after filing this application, in either this application or in a continuing application.

It should be understood that any methods disclosed herein, along with the order in which the respective elements of any such method are performed, are purely exemplary. Depending on the implementation, they may be performed in any order or in parallel, unless indicated otherwise in the present disclosure.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. An analyte detection apparatus configured for testing a substance for the presence or absence of at least one target analyte, the apparatus comprising:
   a housing;
   a mixing chamber positioned within the housing, the mixing chamber temporarily storing a volume of the substance and a volume of a delivery fluid;
   a testing chamber positioned within the housing and in selective fluid communication with the mixing chamber, the testing chamber containing a test medium therewithin for visually indicating the presence or absence of the at least one target analyte within the substance;
   a scoop storage chamber positioned within the housing, the scoop storage chamber separate from the mixing chamber and containing no fluid therewithin;
   a first end of the housing providing a first chamber opening in fluid communication with the scoop storage chamber and a separate second chamber opening in fluid communication with the mixing chamber, the first and second chamber openings providing access to the scoop storage chamber and mixing chamber, respectively;
   an end cap removably engageable with the first end of the housing for creating a fluid-tight and pressurized seal therebetween;
   an elongate collection scoop integral with and extending substantially perpendicularly from an engagement end of the end capm the collection scoop providing at least one substance receptacle recessed within the collection scoop for receiving an appropriate volume of the substance;
   the end cap removably engageable with the first end of the housing in each of a first cap orientation—wherein the collection scoop extends through the first chamber opening so as to be positioned within the scoop storage chamber—and a second cap orientation—wherein the collection scoop extends through the second chamber opening so as to be positioned within the mixing chamber;
   the mixing chamber providing a mixing aperture;
   the testing chamber providing a testing aperture in selective fluid communication with the mixing aperture;
   a mixing valve positioned inline between the mixing aperture and the testing aperture within the housing, the mixing valve rotatably engaged with the housing for selectively rotating between one of an open position—wherein the mixing valve is circumferentially rotated relative to the housing so as to place the mixing aperture in fluid communication with the testing aperture, allowing an appropriate volume of the substance to travel through each of the mixing aperture and testing aperture and into the testing chamber—and a closed position—wherein the mixing valve is circumferentially rotated relative to the housing so as to obstruct fluid communication between the mixing aperture and testing aperture; and
   the housing providing at least one result window which provides visual access into the testing chamber;
   whereby, during use of the apparatus, with the end cap engaged with the first end of the housing in the first cap orientation, the end cap is disengaged from the first end of the housing, an appropriate volume of the substance is collected via the at least one substance receptacle of the collection scoop, the end cap is re-engaged with the first end of the housing in the second cap orientation, thereby introducing the volume of substance from the collection scoop into the mixing chamber, the substance is mixed with the delivery fluid within the mixing chamber, and the mixing valve is rotated into the open position, allowing an appropriate volume of the substance to travel into the testing chamber and come into contact with the test medium, with a resulting visual indication from the test medium being viewable via the at least one result window.

2. The analyte detection apparatus of claim 1, wherein a sidewall of the housing provides a relatively planar surface positioned and configured for preventing the housing from unintentionally rolling when placed on an uneven surface.

3. The analyte detection apparatus of claim 1, wherein:
   the mixing chamber is positioned substantially adjacent to the scoop storage chamber within the housing; and
   the first chamber opening is positioned substantially adjacent to the second chamber opening.

4. The analyte detection apparatus of claim 3, wherein:
   the mixing chamber and scoop storage chamber are positioned in a substantially side-by-side arrangement within the housing; and
   the first chamber opening and second chamber opening are positioned in a substantially side-by-side arrangement.

5. The analyte detection apparatus of claim 1, wherein the engagement end of the end cap is frictionally engageable with the first end of the housing, thereby providing a fluid-tight and pressurized seal between the engagement end of the end cap and one or both of the first and second chamber openings.

6. The analyte detection apparatus of claim 5, wherein the first end of the housing provides an O-ring, gasket or other type of sealing membrane positioned and configured for creating the fluid-tight seal between the engagement end of the end cap and one or both of the first and second chamber openings.

7. The analyte detection apparatus of claim 1, wherein the at least one substance receptacle is positioned proximal to a terminal end of the collection scoop.

8. The analyte detection apparatus of claim 1, wherein the end cap further provides a relatively flat grip portion positioned substantially opposite to the engagement end.

9. The analyte detection apparatus of claim 1, wherein the mixing chamber receives the collection scoop therewithin when the end cap is engaged with the first end of the housing in the second cap orientation.

10. The analyte detection apparatus of claim 1, wherein the scoop storage chamber receives the collection scoop therewithin when the end cap is engaged with the first end of the housing in the first cap orientation.

11. The analyte detection apparatus of claim 1, wherein a sidewall of the housing, along with at least a portion of the mixing chamber, is transparent or translucent, thereby providing visual access into the mixing chamber.

12. The analyte detection apparatus of claim 1, wherein the test medium is a lateral flow test strip.

13. The analyte detection apparatus of claim 12, wherein a sample pad of the test strip is positioned substantially adjacent to the testing aperture.

14. The analyte detection apparatus of claim 1, wherein the test medium is positioned substantially adjacent to the testing aperture so as to come into contact with the substance as the volume of the substance enters the testing chamber when the mixing valve is in the open position.

15. The analyte detection apparatus of claim 1, wherein one or both of the mixing aperture and testing aperture provides an O-ring, gasket or other type of sealing membrane positioned and configured for creating a fluid-tight seal between the mixing chamber and the testing chamber when the mixing valve is in the closed position.

16. The analyte detection apparatus of claim 1, further comprising a valve knob rotatably engaged with the housing and in mechanical communication with the mixing valve, the valve knob configured for enabling the mixing valve to be manually rotated between the open position and closed position during use of the apparatus.

17. The analyte detection apparatus of claim 16, wherein the valve knob is rotatably engaged with an opposing second end of the housing.

18. An analyte detection apparatus configured for testing a substance for the presence or absence of at least one target analyte, the apparatus comprising:
- a housing;
- a mixing chamber positioned within the housing, the mixing chamber temporarily storing a volume of the substance and a volume of a delivery fluid;
- a testing chamber positioned within the housing and in selective fluid communication with the mixing chamber, the testing chamber containing a test medium therewithin for visually indicating the presence or absence of the at least one target analyte within the substance;
- a scoop storage chamber positioned within the housing, the scoop storage chamber separate from the mixing chamber and containing no fluid therewithin;
- a first end of the housing providing a first chamber opening in fluid communication with the scoop storage chamber and a separate second chamber opening in fluid communication with the mixing chamber, the first and second chamber openings providing access to the scoop storage chamber and mixing chamber, respectively;
- an end cap removably engageable with the first end of the housing for creating a fluid-tight and pressurized seal therebwtween;
- an elongate collection scoop integral with and extending substantially perpendicularly from an engagement end of the end cap, the collection scoop providing at least one substance receptacle recessed within the collection scoop for receiving an appropriate volume of the substance;
- the end cap removably engageable with the first end of the housing in each of a first cap orientation—wherein the collection scoop extends through the first chamber opening so as to be positioned within the scoop storage chamber—and a second cap orientation—wherein the collection scoop extends through the second chamber opening so as to be positioned within the mixing chamber;
- the mixing chamber providing a mixing aperture;
- the testing chamber providing a testing aperture in selective fluid communication with the mixing aperture;
- a mixing valve positioned inline between the mixing aperture and the testing aperture within the housing, the mixing valve rotatably engaged with the housing for selectively rotating between one of an open position—wherein the mixing valve is circumferentially rotated relative to the housing so as to place the mixing aperture in fluid communication with the testing aperture, allowing an appropriate volume of the substance to travel through each of the mixing aperture and testing aperture and into the testing chamber—and a closed position—wherein the mixing valve is circumferentially rotated relative to the housing so as to obstruct fluid communication between the mixing aperture and testing aperture;
- an opposing second end of the housing providing a valve knob rotatably engaged with the housing so as to circumferentially rotate relative to a longitudina midline of the housing, the valve knob in mechanical communication with the mixing valve, for enabling the mixing valve to be manually rotated between the open position and closed position via rotation of the valve knob; and
- the housing providing at least one result window which provides visual access into the testing chamber;
- whereby, during use of the apparatus, with the end cap engaged with the first end of the housing in the first cap orientation, the end cap is disengaged from the first end of the housing, an appropriate volume of the substance is collected via the at least one substance receptacle of the collection scoop, the end cap is re-engaged with the first end of the housing in the second cap orientation, thereby introducing the volume of substance from the collection scoop into the mixing chamber, the substance is mixed with the delivery fluid within the mixing chamber, and the mixing valve is rotated into the open position, allowing an appropriate volume of the substance to travel into the testing chamber and come into contact with the test medium, with a resulting visual indication from the test medium being viewable via the at least one result window.

19. A method for testing a substance for the presence or absence of at least one target analyte using the analyte detection apparatus of claim 1, the method comprising the steps of:

disengaging the end cap of the apparatus from the first end of the housing, thereby removing the collection scoop from the scoop storage chamber of the housing;

collecting a volume of the substance with the at least one substance receptacle of the collection scoop;

re-engaging the end cap with the first end of the housing in the second cap orientation, such that the colleciton scoop extends through the second chamber opening and into the mixing chamber of the housing, thereby introducing the volume of substance from the collection scoop into the mixing chamber;

mixing the substance with the delivery fluid within the mixing chamber; and manually rotating the mixing valve into the open position, allowing a volume of the mixed substance and delivery fluid to travel into the testing chamber of the housing and come into contact with the test medium, with a resulting visual indication from the test medium being viewable via the at least one result window of the housing.

* * * * *